United States Patent
Caskey et al.

(10) Patent No.: US 6,180,337 B1
(45) Date of Patent: *Jan. 30, 2001

(54) DIAGNOSIS OF THE FRAGILE X SYNDROME

(75) Inventors: C. Thomas Caskey; David L. Nelson; Maura Pieretti, all of Houston, TX (US); Stephen T. Warren, Clarkston, GA (US); Ben A. Oostra, Rotterdam (NL); Ying-hui Fu, Houston, TX (US)

(73) Assignee: Baylor College of Medicine, Houston, TX (US)

( * ) Notice: Under 35 U.S.C. 154(b), the term of this patent shall be extended for 0 days.

This patent is subject to a terminal disclaimer.

(21) Appl. No.: 07/751,891

(22) Filed: Aug. 29, 1991

Related U.S. Application Data

(63) Continuation-in-part of application No. 07/705,490, filed on May 24, 1991.

(51) Int. Cl.⁷ .............................. C12Q 1/68; G01N 33/53; C07H 21/02; C07K 14/435

(52) U.S. Cl. .............................. 435/6; 435/7.1; 435/91.2; 536/23.5; 536/24.33; 530/350

(58) Field of Search .................. 435/6, 91.2; 536/27, 536/23.1, 23.5, 24.33; 530/350; 935/77, 78

(56) References Cited

PUBLICATIONS

Vincent et al. Nature vol 349 pp 624–626 Issued Feb. 14, 1991.*
D. Heitz et al Science vol 251 pp 1236–1239 Issued Mar. 8, 1991.*
Ludecke et al. Nature vol 338 pp 348–350 Issued Mar. 23, 1989.*

M. Pieretti, et al., "Absence of Expression of the FMR–1 Gene in Fragile X Syndrome" *Cell* 66:817–822 (1991).*

J.S. Sutcliffe, et al., "DNA methylation represses FMR–1 transcription in fragile X syndrome" *Human Molecular Genetics* 1:397–400 (1992).*

D. Devys, et al., "The FMR–1 protein is cytoplasmic, most abundant in neurons and appears normal in carriers of a fragile X premutation" *Nature Genetics* 4:335–340 (1993).*

H. Siomi, et al., "The Protein Product of the Fragile X Gene, FMR1, Has Characteristics of an RNA–Binding Protein" *Cell* 74:291–298 (1993).*

C. Verheij, et al., "Characterization and localization of the FMR–1 gene product associated with fragile X syndrome" *Nature* 363:722–724 (1993).*

D.P.A. Kuhl, et al., "Fragile X Syndrome Protein FMRP Associates with the Microfilament Fraction of the Cellular Cytoskeleton" Submission to Cell.*

* cited by examiner

*Primary Examiner*—Stephanie Zitomer
(74) *Attorney, Agent, or Firm*—Fulbright & Jaworski LLP

(57) ABSTRACT

A sequence of the FMR-1 gene is disclosed. This sequence and related probes, cosmids and unique repeats are used to detect X-linked diseases and especially the fragile X syndrome. Also, methods using methylation-sensitive restriction endonuclease and PCR primer probes were used to detect X-linked disease.

9 Claims, 15 Drawing Sheets

```
         CTGCAGAAATGGGCGTTCTGGCCCTCGCGAGGCAGTGCGACCTGTCACCGCCCTTCAGCC
                                          primer g▶
  61     TTCCCGCCCTCCACCAAGCCCGCGCACGCCCGGCCCGCGCGTCTGTCTTTCGACCCGGCA
              Eag I         BssHII       BssHII
 121     CCCCGGCCGGTTCCCAGCaGCGCGCATGCgcGCGCTCCCAGGCCACTTGAAGAGAGAGGG
                              SacII              Sau3AI
 181     CGGGGCCGAGGGGCTGAGcCCGCGGGGGGAGGGAACAGCGTTGATCACGTGACGTGGTTT
                                           primer a ▶           ◀primer h
 241     CAGTGTTTACACCCGCAGCGGGCCGGGGGTTCGGCCCTAGTCAGGCGCTCAGCTCCGTTT
                                                      primer c ▶
 301     CgGTTTCACTTCCGGTGGAGGGCCGCCTCTGAGCGGGCGGCGGGCCGACGGCGAGCGCGg
              ◀primer b   end of FMR-1
                             ▽
 361     gcggcggcgg tgacggaggcgccgctgccagggggcgtgcggcagcgcGGCGGCGGCGGC
                    primer d◀                              XhoI
 421     GGCGGCGGCGGCGGCGGCGGCGGCGGCGGCGGCGGGctgggcctcgagcgCCCGCAGCCCA
                                      NheI           primer e▶
 481     CCTCTCGGGCGCGGGCTCCCGGCGCTAGCAGGGCTGAAGAGAAGATGGAGGAGCTGGTGG
                                                 exon boundary   ◀primer f
                                                    ▽
 541     TGGAAGTGCGGGGCTCCAATGGCGCTTTCTACAAGGTACTTGGCTCTAGGGCAGGCCCCA

601     TCTTCGCCCTTCCTTCCCTCCCTTTTCTTCTTGGTGTCGGCGGGAGGCAGGCCCGGGGCC

661     CTCTTCCCGAGCACCGCGCCTGGGTGCCAGGGCACGCTCGGCGGGATGTTGTTgGGAGCG

721     AAGGACTGGACTTGGGGCCTGTTGGAAGCCCCTCTCCGACTCCGAGAGGCCCTAGCGCCT

781     ATCGAAATGAGAGACCAGCGAGGAGAGGGTTCTCTTTCGGCGCCGAGcCCCGCCGGGGTG

841     AGCTGGGGATGGGCGAGGGCCGGCGGCAGGTACTAGAGCCGGGCGGGAAGGGCCGAAATC
                                                              BamHI
 901     GGCGCTAAGTGACGGCGATGGCTTATTCCCCCTTTCCTAAACATCATCTCCCAgCGGGAT

961     CCGGGCCTGTCGTGTGGGTAGTTGTGGAGGAGCGGGGGGCGCTTCAGCCGGGCCgCCTCC

1021     TGCAG
```

Figure 11

SEQUENCE LISTING (1) GENERAL INFORMATION:

(iii) NUMBER OF SEQUENCES: 24

(2) INFORMATION FOR SEQ ID NO: 1:

(i) SEQUENCE CHARACTERISTICS:
      (A) LENGTH: 3765 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1:

```
GACGGAGGCG CCCGTGCCAG GGGGCGTGCG GCAGCGCGGC GGCGGCGGCG GCGGCGGCGG         60

CGGCGGAGGC GGCGGCGGCG GCGGCGGCGG CGGCGGAGGC GGCGGCGGCG GCGGCGGCGG        120

CGGCGGCTGG GCCTCGAGCG CCCGCAGCCC ACCTCTCGGG GGCGGGCTCC CGGCGCTAGC        180

AGGGCTGAAG AGAAGATGGA GGAGCTGGTG GTGGAAGTGC GGGGCTCCAA TGGCGCTTTC        240

TACAAGGCAT TTGTAAAGGA TGTTCATGAA GATTCAATAA CAGTTGCATT TGAAAACAAC        300

TGGCAGCCTG ATAGGCAGAT TCCATTTCAT GATGTCAGAT TCCCACCTCC TGTAGGTTAT        360

AATAAAGATA TAAATGAAAG TGATGAAGTT GAGGTGTATT CCAGAGCAAA TGAAAAAGAG        420

CCTTGCTGTT GGTGGTTAGC TAAAGTGAGG ATGATAAAGG GTGAGTTTTA TGTGATAGAA        480

TATGCAGCAT GTGATGCAAC TTACAATGAA ATTGTCACAA TTGAACGTCT AAGATCTGTT        540

AATCCCAACA AACCTGCCAC AAAAGATACT TTCCATAAGA TCAAGCTGGA TGTGCCAGAA        600

GACTTACGGC AAATGTGTGC CAAAGAGGCG GCACATAAGG ATTTTAAAAA GGCAGTTGGT        660

GCCTTTTCTG TAACTTATGA TCCAGAAAAT TATCAGCTTG TCATTTTGTC CATCAATGAA        720

GTCACCTCAA AGCGAGCACA TATGCTGATT GACATGCACT TTCGGAGTCT GCGCACTAAG        780

TTGTCTCTGA TAATGAGAAA TGAAGAAGCT AGTAAGCAGC TGGAGAGTTC AAGGCAGCTT        840

GCCTCGAGAT TTCATGAACA GTTTATCGTA AGAGAAGATC TGATGGGTCT AGCTATTGGT        900

ACTCATGGTG CTAATATTCA GCAAGCTAGA AAAGTACCTG GGGTCACTGC TATTGATCTA        960

GATGAAGATA CCTGCACATT TCATATTTAT GGAGAGGATC AGGATGCAGT GAAAAAAGCT       1020
```

-continued

```
AGAAGCTTTC TCGAATTTGC TGAAGATGTA ATACAAGTTC CAAGGAACTT AGTAGTAATA   1080

GGAAAAAATG GAAAGCTGAT TCAGGAGATT GTGGACAAGT CAGGAGTTGT GAGGGTGAGG   1140

ATTGAGGCTG AAAATGAGAA AAATGTTCCA CAAGAAGAGG AAATTATGCC ACCAAATTCC   1200

CTTCCTTCCA ATAATTCAAG GGTTGGACCT AATGCCCCAG AAGAAAAAAA ACATTTAGAT   1260

ATAAAGGAAA ACAGCACCCA TTTTTCTCAA CCTAACAGTA CAAAAGTCCA GAGGGGTATG   1320

GTACCATTTG TTTTTGTGGG AACAAAGGAC AGCATCGCTA ATGCCACTGT TCTTTTGGAT   1380

TATCACCTGA ACTATTTAAA GGAAGTAGAC CAGTTGCGTT TGGAGAGATT ACAAATTGAT   1440

GAGCAGTTGC GACAGATTGG AGCTAGTTCT AGACCACCAC CAAATCGTAC AGATAAGGAA   1500

AAAAGCTATG TGACTGATGA TGGTCAAGGA ATGGGTCGAG GTAGTAGACC TTACAGAAAT   1560

AGGGGGCACG GCAGACGCGG TCCTGGATAT ACTTCAGGAA CTAATTCTGA AGCATCAAAT   1620

GCTTCTGAAA CAGAATCTGA CCACAGAGAC GAACTCAGTG ATTGGTCATT AGCTCCAACA   1680

GAGGAAGAGA GGGAGAGCTT CCTGCGCAGA GGAGACGGAC GGCGGCGTGG AGGGGGAGGA   1740

AGAGGACAAG GAGGAAGAGG ACGTGGAGGA GGCTTCAAAG GAAACGACGA TCACTCCCGA   1800

ACAGATAATC GTCCACGTAA TCCAAGAGAG GCTAAAGGAA GAACAACAGA TGGATCCCTT   1860

CAGAATACCT CCAGTGAAGG TAGTCGGCTG CGCACGGGTA AGATCGTAAA CCAGAAGAAA   1920

GAGAAGCCAG ACAGCGTGGA TGGTCAGCAA CCACTCGTGA ATGGAGTACC CTAAACTGCA   1980

TAATTCTGAA GTTATATTTC CTATACCATT TCCGTAATTC TTATTCCATA TTAGAAAACT   2040

TTGTTAGGCC AAAGACAAAT AGTAGGCAAG ATGGCACAGG GCATGAAATG AACACAAATT   2100

ATGCTAAGAA TTTTTTATTT TTTGGTATTG CCATAAGCA ACAATTTTCA GATTTGCACA   2160

AAAAGATACC TTAAAATTTG AAACATTGCT TTTAAAACTA CTTAGCACTT CAGGGCAGAT   2220

TTTAGTTTTA TTTTCTAAAG TACTGAGCAG TGATATTCTT TGTTAATTTG GACCATTTTC   2280

CTGCATTGGG TGATCATTCA CCAGTACATT CTCAGTTTTT CTTAATATAT AGCATTTATG   2340

GTAATCATAT TAGACTTCTG TTTTCAATCT CGTATAGAAG TCTTCATGAA ATGCTATGTC   2400

ATTTCATGTC CTGTGTCAGT TTATGTTTTG GTCCACTTTT CCAGTATTTT AGTGGACCCT   2460

GAAATGTGTG TGATGTGACA TTTGTCATTT TCATTAGCAA AAAAAGTTGT ATGATCTGTG   2520

CCTTTTTTAT ATCTTGGCAG GTAGGAATAT TATATTTGGA TGCAGAGTTC AGGGAAGATA   2580

AGTTGGAAAC ACTAAATGTT AAAGATGTAG CAAACCCTGT CAAACATTAG TACTTTATAG   2640

AAGAATGCAT GCTTTCCATA TTTTTTTCCT TACATAAACA TCAGGTTAGG CAGTATAAAG   2700

AATAGGACTT GTTTTTGTTT TTGTTTTGTT GCACTGAAGT TTGATAAAATA GTGTTATTGA   2760

GAGAGATGTG TAATTTTTCT GTATAGACAG GAGAAGAAAG AACTATCTTC ATCTGAGAGA   2820

GGCTAAAATG TTTTCAGCTA GGAACAAATC TTCCTGGTCG AAAGTTAGTA GGATATGCCT   2880

GCTCTTTGGC CTGATGACCA ATTTTAACTT AGAGCTTTTT TTTTAATTT TGTCTGCCCC   2940

AAGTTTTGTG AAATTTTTCA TATTTTAATT TCAAGCTTAT TTTGGAGAGA TAGGAAGGTC   3000

ATTTCCATGT ATGCATAATA ATCCTGCAAA GTACAGGTAC TTTGTCTAAG AAACATTGGA   3060

AGCAGGTTAA ATGTTTTGTA AACTTTGAAA TATATGGTCT AATGTTTAAG CAGAATTGGA   3120

AAAGACTAAG ATCGGTTAAC AAATAACAAC TTTTTTTCT TTTTTCTTT TGTTTTTGA   3180

AGTGTTGGGG TTTGGTTTTG TTTTTTGAGT CTTTTTTTTT TAAGTGAAAT TTATTGAGGA   3240

AAATATGTG AAGGACTTC ACTCTAAGAT GTTATATTTT TCTTAAAAAG TAACTCCTAG   3300

TAGGGGTACC ACTGAATCTG TACAGAGCCG TAAAAACTGA AGTTCTGCCT CTGATGTATT   3360
```

-continued

| | |
|---|---|
| TTGTGAGTTT GTTTCTTTGA ATTTTCATTT TACAGTTACT TTTCCTTGCA TACAAACAAG | 3420 |
| CATATAAAAT GGCAACAAAC TGCACATGAT TTCACAAATA TTAAAAAGTC TTTTAAAAAG | 3480 |
| TATTGCCAAA CATTAATGTT GATTTCTAGT TATTTATTCT GGGAATGTAT AGTATTTGAA | 3540 |
| AACAGAAATT GGTACCTTGC ACACATCATC TGTAAGCTGT TTGGTTTTAA AATACTGTAG | 3600 |
| ATAATTAACC AAGGTAGAAT GACCTTGTAA TGTAACTGCT CTTGGGCAAT ATTCTCTGTA | 3660 |
| CATATTAGCG ACAACAGATT GGATTTTATG TTGACATTTG TTTGGTTATA GTGCAATATA | 3720 |
| TTTTGTATGC AAGCAGTTTC AATAAAGTTT GATCTTCCTC TGCTA | 3765 |

(2) INFORMATION FOR SEQ ID NO: 2:

(i) SEQUENCE CHARACTERISTICS:
        (A) LENGTH: 4188 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 2:

| | |
|---|---|
| ACTTGGAGGG GTATAATCAT TCTAATCAAT GTGTCCCCTT TTACTATAAT ACATTGGAGT | 60 |
| TGCAGCTAAT GCTCTGCTCC CATTCAGCCT ATGATGAGAT TCTCTTTCAG CCCTATTGGG | 120 |
| TTCTTGGCCT CATGTGACTA CTCCAAAGAC CCTAGTCCAA AAGGTCTTTC CTGTTTGCTA | 180 |
| TGGCCTTGAG GAATGTGGCC CTAGATCCAC CGCTTTAAAG CTGGAGTTCC ACCAGCAGCA | 240 |
| ACATCCTCTC ATTCTGGGGC ACCTGCCTGG GGCAGGTCAT CCTGCCTCTG CCAACTCAGT | 300 |
| GCTATTAGTT AACTCTCACC TGCCATATTC CAGCTGGAAT CATCTCCCCT TCTCCACCCC | 360 |
| AGACTAGGTC ATGTTCCGCC ATCATGGAAG CGCCTATTCT TCATACCCCT TATCACAGCT | 420 |
| GCAACTACTC ATTTACTTGT CTGACAATTT GATTTATGTC CACCTACTTT GCTAGGTACT | 480 |
| AAGTTCAATG CTGGCAGTCG TTTCTTCTTT TTTTTTCTTT TCTGTTTTGC TCACCGATTT | 540 |
| CTCGTTAGCA CTTAGCACAG TGTCTGGCAC ACGATAGATG CTCCGTCAAC TTCTCAGTTG | 600 |
| GATACCAGCA TCCCGAAGGG ACATGGATTA AGGCAGCTAT AAGCACGGTG TAAAAACAGG | 660 |
| AATAAGAAAA AGTTGAGGTT TGTTTCACAG TGGAATGTAA AGGGTTGCAA GGAGGTGCAT | 720 |
| CGGCCCCTGT GGACAGGACG CATGACTGCT ACACACGTGT TCACCCCACC CTCTGGCACA | 780 |
| GGGTGCACAT ACAGTAGGGG CAGAAATGAA CCTCAAGTGC TTAACACAAT TTTTAAAAAA | 840 |
| TATATAGTCA AGTGAAAGTA TGAAAATGAG TTGAGGAAAG GCGAGTACGT GGGTCAAAGC | 900 |
| TGGGTCTGAG GAAAGGCTCA CATTTTGAGA TCCCGACTCA ATCCATGTCC CTTAAAGGGC | 960 |
| ACAGGGTGTC TCCACAGGGC CGCCCAAAAT CTGGTGAGAG AGGGCGTAGA CGCCTCACCT | 1020 |
| TCTGCCTCTA CGGGTCACAA AAGCCTGGGT CACCCTGGTT GCCACTGTTC CTAGTTCAAA | 1080 |
| GTCTTCTTCT GTCTAATCCT TCACCCCTAT TCTCGCCTTC CACTCCACCT CCCGCTCAGT | 1140 |
| CAGACTGCGC TACTTTGAAC CGGACCAAAC CAAACCAAAC CAAACCAAAC CAAACCAGAC | 1200 |
| CAGACACCCC CTCCCGCGGA ATCCCAGAGA GGCCGAACTG GGATAACCGG ATGCATTTGA | 1260 |
| TTTCCCACGC CACTGAGTGC ACCTCTGCAG AAATGGGCGT TCTGGCCCTC GCGAGGCAGT | 1320 |
| GCGACCTGTC ACCGCCCTTC AGCCTTCCCG CCCTCCACCA AGCCCGCGCA CGCCCGGCCC | 1380 |
| GCGCGTCTGT CTTTCGACCC GGCACCCCGG CCGGTTCCCA GCAGCGCGCA TGCGCGCGCT | 1440 |
| CCCAGGCCAC TTGAAGAGAG AGGGCGGGGC CGAGGGGCTG AGCCCGCGGG GGGAGGGAAC | 1500 |

```
-continued

AGCGTTGATC ACGTGACGTG GTTTCAGTGT TTACACCCGC AGCGGGCCGG GGGTTCGGCC    1560

TCAGTCAGGC GCTCAGCTCC GTTTCGGTTT CACTTCCGGT GGAGGGCCGC CTCTAGCGGG    1620

CGGCGGGCCG ACGGCGAGCG CGGGCGGCGG CGGTGACGGA GGCGCCGCTG CCAGGGGGCG    1680

TGCGGCAGCG CGGCGGCGGC GGCGGCGGCG GCGGCGGCGG CGGCGGCGGC GGCGGCGGCT    1740

GGGCCTCGAG CGCCCGCAGC CCACCTCTTG GGGGCGGGCT CCCGGCGCTA CAGGGCTGAA    1800

GAGAAGATGG AGGAGCTGGT GGTGGAAGTG CGGGCTCCAA TGGCGCTTTC TACAAGGTAC    1860

TTGGCTCTAG GCAGGCCCC ATCTTCGCCC TTCCTTCCCT CCCTTTTTTC TTGGTGTCGG    1920

CGGGAGGCAG GCCCGGGCC CTCTTCCCGA GCACCGCGCC TGGGTGCCAG GCACGCTCG    1980

GCGGGATGTT GTTGGGAGGG AAGGACTGGA CTTGGGGCCT GTTGGAAGCC CCTCTCCGAC    2040

TCCAGAGGCC CTAGCGCCTA TCGAAATGAG AGACCAGCGA GGAGAGGGTT CTCTTTCGGC    2100

GCCGAGCCCC GCCGGGGTGA GCTGGGGATG GGCGAGGGCC GGCGGCAGGT ACTAGAGCCG    2160

GGCGGGAAGG GCCGAAATCG GCGCTAAGTG ACGGCGATGG CTTATTCCCC CTTTCCTAAA    2220

CATCATCTCC CAGCGGGATC CGGGCCTGTC GTGTGGGTAG TTGTGGAGGA GCGGGGGCG    2280

CTTCAGCCGG GCCGCCTCCT GCAGCGCCAA GAGGGCTTCA GGTCTCCTTT GGCTTCTCTT    2340

TTCCGGTCTA GCATTGGGAC TTCGGAGAGC TCCACTGTTC TGGGCGAGGG CTGTGAAGAA    2400

AGAGTAGTAA GAAGCGGTAG TCGGCACCAA ATCACAATGG CAACTGATTT TTAGTGGCTT    2460

CTCTTTGTGG ATTTCGGAGG AGATTTTAGA TCCAAAAGTT TCAGGAAGAC CTAACATGG    2520

CCCAGCAGTG CATTGAAGAA GTTGATCATC GTGAATATTC GCGTCCCCCT TTTTGTTAAA    2580

CGGGGTAAAT TCAGGAATGC ACATGCTTCA GCGTCTAAAA CCATTAGCAG CGCTGCTACT    2640

TAAAAATTGT GTGTGTGTGT TTAAGTTTCC AAAGACCTAA ATATATGCCA TGAAACTTCA    2700

GGTAATTAAC TGAGAGTATA TTATTACTAG GGCATTTTTT TTTTAACTGA GCGAAAATAT    2760

TTTTGTGCCC CTAAGAACTT GACCACATTT CCTTTGAATT TGTGGTGTTG CAGTGGACTG    2820

AATTGTTGAG GCTTTATATA GGCATTCATG GGTTTACTGT GCTTTTTAAA GTTACACCAT    2880

TGCAGATCAA CTAACACCTT TCAGTTTTAA AAGGAAGATT TACAAATTTG ATGTAGCAGT    2940

AGTGCGTTTG TTGGTATGTA GGTGCTGTAT AAATTCATCT ATAAATTCTC ATTTCCTTTT    3000

GAATGTCTAT AACCTCTTTC AATAATATCC CACCTTACTA CAGTATTTTG GCAATAGAAG    3060

GTGCGTGTGG AAGGAAGGCT GGAAAATAGC TATTAGCAGT GTCCAACACA ATTCTTAAAT    3120

GTATTGTAGA ATGGCTTGAA TGTTTCAGAC AGGCACGTT TGGCTATAGG AAAATAAACA    3180

ATTGACTTTA TTCTGTGTTT ACCAATTTTA TGAAGACATT TGGAGATCAG TATATTTCAT    3240

AAATGAGTAA AGTATGTAAA CTGTTCCATA CTTTGAGCAC AAAGATAAAG CCTTTTGCTG    3300

TAAAAGGAGG CAAAAGGTAA CCCCGCGTTT ATGTTCTTAA CAGTCTCATG AATATGAAAT    3360

TGTTTCAGTT GACTCTGCAG TCAAAATTTT AATTTCATTG ATTTTATTGA TCCATAATTT    3420

CTTCTGGTGA GTTTGCGTAG AATCGTTCAC GGTCCTAGAT TAGTGGTTTT GGTCACTAGA    3480

TTTCTGGCAC TAATAACTAT AATACATATA CATATATATG TGTGAGTAAC GGCTAATGGT    3540

TAGGCAAGAT TTTGATTGAC CTGTGATATA AACTTAGATT GGATGCCACT AAAGTTTGCT    3600

TATCACAGAG GGCAAGTAGC ACATTATGGC CTTGAAGTAC TTATTGTTCT CTTCCAGCAA    3660

CTTATGATTT GCTCCAGTGA TTTTCTTGCA CACTGACTGG AATATAAGAA ATGCCTTCTA    3720

TTTTTGCTAT TAATTCCCTC CTTTTTTGTT TTGTTTTGTA ACGAAGTTGT TAACTTGAA    3780

GGTGAATGAA GAATAGGTTG GTTGCCCCTT AGTTCCCTGA GGAGAAATGT TAATACTTGA    3840

ACAAGTGTGT GTCAGACAAA TTGCTGTTAT GTTTATTTAA TTAAGTTTGA TTTCTAAGAA    3900
```

```
AATCTCAAAT GGTCTGCACT GATGGAAGAA CAGTTTCTGT AACAAAAAAG CTTGAAATTT      3960

TTATATGACT TATAATACTG CTGTGAGTTT TAAAAGTAAA GCAAAAGTAA ACTGAGTTGC      4020

TTGTCCAGTG GGATGGACAG GAAAGATGTG AAATAAAAAC CAATGAAAAA TGAACTGCTG      4080

TGGAGAAGTG TTACATTTAT GGAAAAAGAA ATAGGAACCT TGTTCATCAA ATTGATAGAA      4140

AAGCTTTTAA AACTAAACAA ATCAAACAAC TTGAGTATAA TGGAATTC                   4188

(2) INFORMATION FOR SEQ ID NO: 3:

(i) SEQUENCE CHARACTERISTICS:
         (A) LENGTH: 229 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (xi) SEQUENCE DESCRIPTION: SEQ ID NO: 3:

GAATTCAGGT AAGCTATCTT GAAAGGGGAA ATATCAAAAG CTAGAGATCA GAGTAAGGCT        60

GAGACTCAGA GTCAAGTGGG GAAGACTAAG TTGCAGTATG TACTGGCAGT GAAGATAAGT       120

ATTTATTCAT TCATTGAACA TACCTTGAAA TCAACCACTT TTAATGTGCC AGGGACACAA       180

AGATAGAAAA GACATTTGCC CTGTCTGGAA GGTACTAATA ATCCAATAA                   229

(2) INFORMATION FOR SEQ ID NO: 4:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (xi) SEQUENCE DESCRIPTION: SEQ ID NO: 4:

CTTGCCAACC GTTCAGCCAC                                                    20

(2) INFORMATION FOR SEQ ID NO: 5:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (xi) SEQUENCE DESCRIPTION: SEQ ID NO: 5:

ATTTCCTGGA GCACAGACTG                                                    20

(2) INFORMATION FOR SEQ ID NO: 6:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (genomic)
```

```
        (iii) HYPOTHETICAL: NO (xi) SEQUENCE DESCRIPTION: SEQ ID NO: 6:

AGAGCTTCAC TATGCAATGG AATC                                              24

(2) INFORMATION FOR SEQ ID NO: 7:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (xi) SEQUENCE DESCRIPTION: SEQ ID NO: 7:

GTACATTAGA GTCACCTGTG GTGC                                              24

(2) INFORMATION FOR SEQ ID NO: 8:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (xi) SEQUENCE DESCRIPTION: SEQ ID NO: 8:

TAGCTAACCA CCAACAGCAA GGC                                               23

(2) INFORMATION FOR SEQ ID NO: 9:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (xi) SEQUENCE DESCRIPTION: SEQ ID NO: 9:

AACTGGCAGC CTGATAGGCA GATTC                                             25

(2) INFORMATION FOR SEQ ID NO: 10:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (xi) SEQUENCE DESCRIPTION: SEQ ID NO: 10:

GCTCAGCTCC GTTTCGGTTT CACTTCCGGT                                        30

(2) INFORMATION FOR SEQ ID NO: 11:

(i) SEQUENCE CHARACTERISTICS:
             (A) LENGTH: 30 base pairs
```

(B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 11:

AGCCCCGCAC TTCCACCACC AGCTCCTCCA                                              30

(2) INFORMATION FOR SEQ ID NO: 12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 12:

CGTGGGGTCC TTTTCACCAG CAAG                                                    24

(2) INFORMATION FOR SEQ ID NO: 13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 13:

AATTATGGAC AGGACTGAAC GTC                                                     23

(2) INFORMATION FOR SEQ ID NO: 14:

(i) SEQUENCE CHARACTERISTICS:
        (A) LENGTH: 657 amino acids
        (B) TYPE: amino acid
        (D) TOPOLOGY: linear (ii) MOLECULE TYPE: peptide (iii) HYPOTHETICAL: YES (v) FRAGMENT TYPE: C-terminal (xi) SEQUENCE DESCRIPTION: SEQ ID NO: 14:

Asp Gly Gly Ala Arg Ala Arg Gly Arg Ala Ala Ala Arg Arg Arg
1               5                  10                  15

Arg Arg Arg Arg Arg Arg Arg Arg Arg Arg Arg Arg Arg Arg Arg
            20                  25                  30

Arg Arg Arg Arg Arg Arg Arg Arg Arg Leu Gly Leu Glu Arg Pro
            35                  40                  45

Gln Pro Thr Ser Arg Gly Arg Ala Pro Gly Ala Ser Arg Ala Glu Glu
        50                  55                  60

Lys Met Glu Glu Leu Val Val Glu Val Arg Gly Ser Asn Gly Ala Phe
65                  70                  75                  80

Tyr Lys Ala Phe Val Lys Asp Val His Glu Asp Ser Ile Thr Val Ala
                85                  90                  95

-continued

```
Phe Glu Asn Asn Trp Gln Pro Asp Arg Gln Ile Pro Phe His Asp Val
            100                 105                 110
Arg Phe Pro Pro Val Gly Tyr Asn Lys Asp Ile Asn Glu Ser Asp
        115                 120                 125
Glu Val Glu Val Tyr Ser Arg Ala Asn Glu Lys Glu Pro Cys Cys Trp
        130                 135                 140
Trp Leu Ala Lys Val Arg Met Ile Lys Gly Glu Phe Tyr Val Ile Glu
145                 150                 155                 160
Tyr Ala Ala Cys Asp Ala Thr Tyr Asn Glu Ile Val Thr Ile Glu Arg
                165                 170                 175
Leu Arg Ser Val Asn Pro Asn Lys Pro Ala Thr Lys Asp Thr Phe His
            180                 185                 190
Lys Ile Lys Leu Asp Val Pro Glu Asp Leu Arg Gln Met Cys Ala Lys
            195                 200                 205
Glu Ala Ala His Lys Asp Phe Lys Lys Ala Val Gly Ala Phe Ser Val
            210                 215                 220
Thr Tyr Asp Pro Glu Asn Tyr Gln Leu Val Ile Leu Ser Ile Asn Glu
225                 230                 235                 240
Val Thr Ser Lys Arg Ala His Met Leu Ile Asp Met His Phe Arg Ser
                245                 250                 255
Leu Arg Thr Lys Leu Ser Leu Ile Met Arg Asn Glu Glu Ala Ser Lys
                260                 265                 270
Gln Leu Glu Ser Ser Arg Gln Leu Ala Ser Arg Phe His Glu Gln Phe
            275                 280                 285
Ile Val Arg Glu Asp Leu Met Gly Leu Ala Ile Gly Thr His Gly Ala
            290                 295                 300
Asn Ile Gln Gln Ala Arg Lys Val Pro Gly Val Thr Ala Ile Asp Leu
305                 310                 315                 320
Asp Glu Asp Thr Cys Thr Phe His Ile Tyr Gly Glu Asp Gln Asp Ala
                325                 330                 335
Val Lys Lys Ala Arg Ser Phe Leu Glu Phe Ala Glu Asp Val Ile Gln
            340                 345                 350
Val Pro Arg Asn Leu Val Val Ile Gly Lys Asn Gly Lys Leu Ile Gln
            355                 360                 365
Glu Ile Val Asp Lys Ser Gly Val Val Arg Val Arg Ile Glu Ala Glu
            370                 375                 380
Asn Glu Lys Asn Val Pro Gln Glu Glu Ile Met Pro Pro Asn Ser
385                 390                 395                 400
Leu Pro Ser Asn Asn Ser Arg Val Gly Pro Asn Ala Pro Glu Glu Lys
                405                 410                 415
Lys His Leu Asp Ile Lys Glu Asn Ser Thr His Phe Ser Gln Pro Asn
            420                 425                 430
Ser Thr Lys Val Gln Arg Gly Met Val Pro Phe Val Phe Val Gly Thr
            435                 440                 445
Lys Asp Ser Ile Ala Asn Ala Thr Val Leu Leu Asp Tyr His Leu Asn
            450                 455                 460
Tyr Leu Lys Glu Val Asp Gln Leu Arg Leu Glu Arg Leu Gln Ile Asp
465                 470                 475                 480
Glu Gln Leu Arg Gln Ile Gly Ala Ser Ser Arg Pro Pro Asn Arg
                485                 490                 495
Thr Asp Lys Glu Lys Ser Tyr Val Thr Asp Asp Gly Gln Gly Met Gly
            500                 505                 510
```

Arg Gly Ser Arg Pro Tyr Arg Asn Arg Gly His Gly Arg Arg Gly Pro
            515                 520                 525

Gly Tyr Thr Ser Gly Thr Asn Ser Glu Ala Ser Asn Ala Ser Glu Thr
        530                 535                 540

Glu Ser Asp His Arg Asp Glu Leu Ser Asp Trp Ser Leu Ala Pro Thr
545                 550                 555                 560

Glu Glu Glu Arg Glu Ser Phe Leu Arg Arg Gly Asp Gly Arg Arg Arg
                565                 570                 575

Gly Gly Gly Gly Arg Gly Gln Gly Gly Arg Gly Arg Gly Gly Gly Phe
            580                 585                 590

Lys Gly Asn Asp Asp His Ser Arg Thr Asp Asn Arg Pro Arg Asn Pro
            595                 600                 605

Arg Glu Ala Lys Gly Arg Thr Thr Asp Gly Ser Leu Gln Asn Thr Ser
    610                 615                 620

Ser Glu Gly Ser Arg Leu Arg Thr Gly Lys Asp Arg Asn Gln Lys Lys
625                 630                 635                 640

Glu Lys Pro Asp Ser Val Asp Gly Gln Gln Pro Leu Val Asn Gly Val
                645                 650                 655

Pro (2) INFORMATION FOR SEQ ID NO: 15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 15:

GGAACAGCGT TGATCACGTG ACGTGGTTTC                                          30

(2) INFORMATION FOR SEQ ID NO: 16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

ACCGGAAGTG AAACCGAAAC GGAGCTGAGC                                          30

(2) INFORMATION FOR SEQ ID NO: 17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

GCACGCCCCC TGGCAGCGGC GCCTCCGTCA                                          30

(2) INFORMATION FOR SEQ ID NO: 18:

```
    (i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

TGGGCCTCGA GCGCCCGCAG CCCACCTCTC                                    30

(2) INFORMATION FOR SEQ ID NO: 19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

AGTGCGACCT GTCACCGCCC TTCAGCCTTC                                    30

(2) INFORMATION FOR SEQ ID NO: 20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

GAAACCACGT CACGTGATCA ACGCTGTTCC                                    30

(2) INFORMATION FOR SEQ ID NO: 21:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

ACCAGGTAGC CTGTGGGGCC TCTACGATGG GC                                 32

(2) INFORMATION FOR SEQ ID NO: 22:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

CCAGAGCGTG CGCGAAGTGA TCCAGAACCC GG                                 32

(2) INFORMATION FOR SEQ ID NO: 23:

(i) SEQUENCE CHARACTERISTICS:
        (A) LENGTH: 5222 base pairs
        (B) TYPE: nucleic acid
        (C) STRANDEDNESS: single
```

(D) TOPOLOGY: linear (ii) MOLECULE TYPE: DNA (genomic)

(xi) SEQUENCE DESCRIPTION: SEQ ID NO: 23:

```
GAATTCAGGT AAGCTATCTT GAAAGGGAA ATATCAAAAG CTAGAGATCA GAGTAAGGCT      60
GAGACTCAGA GTCAAGTGGG GAAGACTAAG TTGCAGTATG TACTGGCAGT GAAGATAAGT     120
ATTTATTCAT TCATTGAACA TACCTTGAAA TCAACCACTT TTAATGTGCC AGGGACACAA     180
AGATAGAAAA GACATTTGCC CTGTCTGGAA GGTACTAATA ATCCAATAAG GAAAACAGAA     240
ATATAAATAA ATTATTCTAG TACACTAACC ATCATAGTAG AGGTATTCAA CATTTGTTGA     300
GTCTCTGCTA TATGCCAAGC AGTGTAATGA GGAAGCAGAG GGTATGCACA AAGTTCTACA     360
AGAGCACAAA ATAAGTTCTG GCAAAGGTTT GTAAAGACAT TCACAAGGGT TTTCACCACA     420
GTATGACTTC AGGGAGTTGG CAGTAACCTA GATGCCCGAT CAGTAGGGAT ATGTATGAAT     480
AAAATTTCTG GCATACTCGG TAGCAAACTA GGTGTACACA CAGCAATGTG GGTATAGCTC     540
AAAAACAGAC TGTTGAGTAA AACAGTGGGA AATAGAGATT TACAGTCCAA TACCATCTCT     600
GTAAATGCAA GAGGCATAAA CAAAACATTA TCTGTGTTAA ATTATCAAGG ATCTCTATCG     660
AACATATTGC AGCTTGTGTC TAGAAGAATG AGAGTGGGGA TCGAGAAAGA TGAGGAAAAA     720
ATAATATAAA CACTATAAAA TAATGTAAAC AAGGACCCTG TAGGGACTGA TATGACAATG     780
TGCTGAAAAT TGAGGAGCAA AGTTAACTCT CTGTACCTGA GATAAAATAA CTAGCTAATA     840
GGAATCCAGC TGAAAACCTT AAGGTGCAGG GCCTCTATGG GGCCCAGGAA GGATGTGTAG     900
AGACATGAAC GGATGAAAGT GCATCACAGG TTCAGGGAAC AACACAGGTT GAGTGTGGCT     960
TGTAGTAAAA ATGGTTGTGA AGAGTTGACA TATTTTAAG CCCTGGGTAA ATTGAACAAC     1020
AGCTTACACT TGGAGGGGTA TAATCATTCT AATCAATGTG TCCCCTTTTA CTATAATACA    1080
TTGGAGTTGC AGCTAATGCT CTGCTCCCAT TCAGCCTATG ATGAGATTCT CTTTCAGCCC    1140
TATTGGGTTC TTGGCCTCAT GTGACTACTC CAAAGACCCT AGTCCAAAAG GTCTTTCCTG    1200
TTTGCTATGG CCTTGAGGAA TGTGGCCCTA GATCCACCGC TTTAAAGCTG GAGTTCCACC    1260
AGCAGCAACA TCCTCTCATT CTGGGGCACC TGCCTGGGGC AGGTCATCCT GCCTCTGCCA    1320
ACTCAGTGCT ATTAGTTAAC TCTCACCTGC CATATTCCAG CTGGAATCAT CTCCCCTTCT    1380
CCACCCCAGA CTAGGTCATG TTCCGCCATC ATGGAAGCGC CTATTCTTCA TACCCCTTAT    1440
CACAGCTGCA ACTACTCATT TACTTGTCTG ACAATTTGAT TTATGTCCAC CTACTTTGCT    1500
AGGTACTAAG TTCAATGCTG GCAGTCGTTT CTTCTTTTTT TTTCTTTTCT GTTTTGCTCA    1560
CCGATTTCTC GTTAGCACTT AGCACAGTGT CTGGCACACG ATAGATGCTC CGTCAACTTC    1620
TCAGTTGGAT ACCAGCATCC CGAAGGGGAC ATGGATTAAG GCAGCTATAA GCACGGTGTA    1680
AAAACAGGAA TAAGAAAAAG TTGAGGTTTG TTTCACAGTG GAATGTAAAG GGTTGCAAGG    1740
AGGTGCATCG GCCCCTGTGG ACAGGACGCA TGACTGCTAC ACACGTGTTC ACCCCACCCT    1800
CTGGCACAGG GTGCACATAC AGTAGGGGCA GAAATGAACC TCAAGTGCTT AACACAATTT    1860
TTAAAAAATA TATAGTCAAG TGAAAGTATG AAAATGAGTT GAGGAAAGGC GAGTACGTGG    1920
GTCAAAGCTG GGTCTGAGGA AAGGCTCACA TTTTGAGATC CCGACTCAAT CCATGTCCCT    1980
TAAAGGGCAC AGGGTGTCTC CACAGGGCCG CCCAAAATCT GGTGAGAGAG GGCGTAGACG    2040
CCTCACCTTC TGCCTCTACG GGTCACAAAA GCCTGGGTCA CCCTGGTTGC CACTGTTCCT    2100
AGTTCAAAGT CTTCTTCTGT CTAATCCTTC ACCCCTATTC TCGCCTTCCA CTCCACCTCC    2160
CGCTCAGTCA GACTGCGCTA CTTTGAACCG GACCAAACCA AACCAAACCA AACCAAACCA    2220
```

-continued

```
AACCAGACCA GACACCCCCT CCCGCGGAAT CCCAGAGAGG CCGAACTGGG ATAACCGGAT      2280

GCATTTGATT TCCCACGCCA CTGAGTGCAC CTCTGCAGAA ATGGGCGTTC TGGCCCTCGC      2340

GAGGCAGTGC GACCTGTCAC CGCCCTTCAG CCTTCCCGCC CTCCACCAAG CCCGCGCACG      2400

CCCGGCCCGC GCGTCTGTCT TTCGACCCGG CACCCCGGCC GGTTCCCAGC AGCGCGCATG      2460

CGCGCGCTCC CAGGCCACTT GAAGAGAGAG GGCGGGCCG AGGGGCTGAG CCCGCGGGGG      2520

GAGGGAACAG CGTTGATCAC GTGACGTGGT TTCAGTGTTT ACACCCGCAG CGGGCCGGGG      2580

GTTCGGCCCT AGTCAGGCGC TCAGCTCCGT TTCGGTTTCA CTTCCGGTGG AGGGCCGCCT      2640

CTGAGCGGGC GGCGGGCCGA CGGCGAGCGC GGGCGGCGGC GGTGACGGAG GCGCCGCTGC      2700

CAGGGGGCGT GCGGCAGCGC GGCGGCGGCG GCGGCGGCGG CGGCGGCGGC GGCGGCGGCG      2760

GCGGCGGCTG GGCCTCGAGC GCCCGCAGCC CACCTCTCGG GGGCGGGCTC CCGGCGCTAG      2820

CAGGGCTGAA GAGAAGATGG AGGAGCTGGT GGTGGAAGTG CGGGGCTCCA ATGGCGCTTT      2880

CTACAAGGTA CTTGGCTCTA GGGCAGGCCC CATCTTCGCC CTTCCTTCCC TCCCTTTTCT      2940

TCTTGGTGTC GGCGGGAGGC AGGCCCGGGG CCCTCTTCCC GAGCACCGCG CCTGGGTGCC      3000

AGGGCACGCT CGGCGGGATG TTGTTGGGAG GGAAGGACTG GACTTGGGGC CTGTTGGAAG      3060

CCCCTCTCCG ACTCCGAGAG GCCCTAGCGC CTATCGAAAT GAGAGACCAG CGAGGAGAGG      3120

GTTCTCTTTC GGCGCCGAGC CCCGCCGGGG TGAGCTGGGG ATGGGCGAGG GCCGGCGGCA      3180

GGTACTAGAG CCGGGCGGGA AGGGCCGAAA TCGGCGCTAA GTGACGGCGA TGGCTTATTC      3240

CCCCTTTCCT AAACATCATC TCCCAGCGGG ATCCGGGCCT GTCGTGTGGG TAGTTGTGGA      3300

GGAGCGGGGG GCGCTTCAGC CGGGCCGCCT CCTGCAGCGC CAAGAGGGCT TCAGGTCTCC      3360

TTTGGCTTCT CTTTTCCGGT CTAGCATTGG GACTTCGGAG AGCTCCACTG TTCTGGGCGA      3420

GGGCTGTGAA GAAAGAGTAG TAAGAAGCGG TAGTCGGCAC CAAATCACAA TGGCAACTGA      3480

TTTTTAGTGG CTTCTCTTTG TGGATTTCGG AGGAGATTTT AGATCCAAAA GTTTCAGGAA      3540

GACCCTAACA TGGCCCAGCA GTGCATTGAA GAAGTTGATC ATCGTGAATA TTCGCGTCCC      3600

CCTTTTTGTT AAACGGGGTA AATTCAGGAA TGCACATGCT TCAGCGTCTA AAACCATTAG      3660

CAGCGCTGCT ACTTAAAAAT TGTGTGTGTG TGTTTAAGTT TCCAAAGACC TAAATATATG      3720

CCATGAAACT TCAGGTAATT AACTGAGAGT ATATTATTAC TAGGGCATTT TTTTTTTAAC      3780

TGAGCGAAAA TATTTTTGTG CCCCTAAGAA CTTGACCACA TTTCCTTTGA ATTTGTGGTG      3840

TTGCAGTGGA CTGAATTGTT GAGGCTTTAT ATAGGCATTC ATGGGTTTAC TGTGCTTTTT      3900

AAAGTTACAC CATTGCAGAT CAACTAACAC CTTTCAGTTT TAAAAGGAAG ATTTACAAAT      3960

TTGATGTAGC AGTAGTGCGT TTGTTGGTAT GTAGGTGCTG TATAAATTCA TCTATAAATT      4020

CTCATTTCCT TTTGAATGTC TATAACCTCT TTCAATAATA TCCCACCTTA CTACAGTATT      4080

TTGGCAATAG AAGGTGCGTG TGGAAGGAAG GCTGGAAAAT AGCTATTAGC AGTGTCCAAC      4140

ACAATTCTTA AATGTATTGT AGAATGGCTT GAATGTTTCA GACAGGACAC GTTTGGCTAT      4200

AGGAAAATAA ACAATTGACT TTATTCTGTG TTTACCAATT TTATGAAGAC ATTTGGAGAT      4260

CAGTATATTT CATAAATGAG TAAAGTATGT AAACTGTTCC ATACTTTGAG CACAAAGATA      4320

AAGCCTTTTG CTGTAAAAGG AGGCAAAAGG TAACCCCGCG TTTATGTTCT TAACAGTCTC      4380

ATGAATATGA AATTGTTTCA GTTGACTCTG CAGTCAAAAT TTTAATTTCA TTGATTTTAT      4440

TGATCCATAA TTTCTTCTGG TGAGTTTGCG TAGAATCGTT CACGGTCCTA GATTAGTGGT      4500

TTTGGTCACT AGATTTCTGG CACTAATAAC TATAATACAT ATACATATAT ATGTGTGAGT      4560
```

-continued

```
AACGGCTAAT GGTTAGGCAA GATTTTGATT GACCTGTGAT ATAAACTTAG ATTGGATGCC      4620

ACTAAAGTTT GCTTATCACA GAGGGCAAGT AGCACATTAT GGCCTTGAAG TACTTATTGT      4680

TCTCTTCCAG CAACTTATGA TTTGCTCCAG TGATTTTGCT TGCACACTGA CTGGAATATA      4740

AGAAATGCCT TCTATTTTTG CTATTAATTC CCTCCTTTTT TGTTTTGTTT TGTAACGAAG      4800

TTGTTTAACT TGAAGGTGAA TGAAGAATAG GTTGGTTGCC CCTTAGTTCC CTGAGGAGAA      4860

ATGTTAATAC TTGAACAAGT GTGTGTCAGA CAAATTGCTG TTATGTTTAT TTAATTAAGT      4920

TTGATTTCTA AGAAAATCTC AAATGGTCTG CACTGATGGA AGAACAGTTT CTGTAACAAA      4980

AAAGCTTGAA ATTTTTATAT GACTTATAAT ACTGCTGTGA GTTTTAAAAG TAAAGCAAAA      5040

GTAAACTGAG TTGCTTGTCC AGTGGGATGG ACAGGAAAGA TGTGAAATAA AAACCAATGA      5100

AAAATGAACT GCTGTGGAGA AGTGTTACAT TTATGGAAAA AGAAATAGGA ACCTTGTTCA      5160

TCAAATTGAT AGAAAAGCTT TTAAAACTAA ACAAATCAAA CAACTTGAGT ATAATGGAAT      5220

TC                                                                    5222
```

(2) INFORMATION FOR SEQ ID NO: 24:

(i) SEQUENCE CHARACTERISTICS:
        (A) LENGTH: 1026 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 24:

```
CTGCAGAAAT GGGCGTTCTG GCCCTCGCGA GGCAGTTGCG ACCTGTCACC GCCCTTCAGC        60

CTTCCCGCCC TCCACCAAGC CCGCGCACGC CCGGCCCGCG CGTCTGTCTT TCGACCCGGC       120

ACCCCGGCCG GTTCCCAGCA GCGCGCATGC GCGCGCTCCC AGGCCACTTG AAGAGAGAGG       180

GCGGGGCCGA GGGGCTGAGC CCGCGGGGGG AGGGAACAGC GTTGATCACG TGACGTGGTT       240

TCAGTGTTTA CACCCGCAGC GGGCCGGGGG TTCGGCCCTA GTCAGGCGCT CAGCTCCGTT       300

TCGGTTTCAC TTCCGGTGGA GGGCCGCCTC TGAGCGGGCG GCGGGCCGAC GGCGAGCGCG       360

GGCGGCGGCG GTGACGGAGG CGCCGCTGCC AGGGGGCGTG CGGCAGCGCG GCGGCGGCGG       420

CGGCGGCGGC GGCGGCGGCG GCGGCGGCGG CGGCGGCTGG GCCTCGAGCG CCCGCAGCCC       480

ACCTCTCGGG GGCGGGCTCC CGGCGCTAGC AGGGCTGAAG AGAAGATGGA GGAGCTGGTG       540

GTGGAAGTGC GGGGCTCCAA TGGCGCTTTC TACAAGGTAC TTGGCTCTAG GGCAGGCCCC       600

ATCTTCGCCC TTCCTTCCCT CCCTTTTCTT CTTGGTGTCG GCGGGAGGCA GGCCCGGGGC       660

CCTCTTCCCG AGCACCGCGC CTGGGTGCCA GGGCACGCTC GGCGGGATGT TGTTGGGAGG       720

GAAGGACTGG ACTTGGGGCC TGTTGGAAGC CCCTCTCCGA CTCCGAGAGG CCCTAGCGCC       780

TATCGAAATG AGAGACCAGC GAGGAGAGGG TTCTCTTTCG GCGCCGAGCC CCGCCGGGGT       840

GAGCTGGGGA TGGGCGAGGG CCGGCGGCAG GTACTAGAGC CGGGCGGGAA GGGCCGAAAT       900

CGGCGCTAAG TGACGGCGAT GGCTTATTCC CCCTTTCCTA AACATCATCT CCCAGCGGGA       960

TCCGGGCCTG TCGTGTGGGT AGTTGTGGAG GAGCGGGGGG CGCTTCAGCC GGGCCGCCTC      1020

CTGCAG                                                                1026
```

DIAGNOSIS OF THE FRAGILE X SYNDROME

This application is a Continuation-In-Part of U.S. Ser. No. 07/705,490 filed May 24, 1991.

This invention was supported by the National Institutes of Health, under grant number LTD 20521. The government may have certain rights under this application.

FIELD OF THE INVENTION

This invention relates to the field of molecular diagnosis of the fragile X syndrome.

BACKGROUND

The fragile X syndrome is the most frequently encountered form of inherited mental retardation in humans and has a prevalence estimated to be 1/1250 males. The fragile X syndrome segregates as an X-linked dominant disorder with reduced penetrance. Either sex when carrying the fragile X mutation may exhibit mental deficiency. It has been shown that approximately 30% of carrier females are penetrant and that 20% of males carrying the fragile X chromosome are normal but may transmit the disorder and have fully penetrant grandsons. In addition to the mental retardation which is variable in severity, penetrant males exhibit additional phenotypic involvement including macroorchidism and distinctive facies. Since fully penetrant males rarely reproduce, it has been suggested that the frequency of new mutations of the fragile X site may be as high as 1/3000 germ cells to maintain the population frequency.

The fragile X syndrome, as implied by its name, is associated with a fragile site expressed as an isochromatid gap in the metaphase chromosome at map position Xq 27.3. The fragile X site is induced by cell culture conditions which perturb deoxypyrimidine pools and is rarely observed in greater than 50% of the metaphase spreads. Neither the molecular nature of the fragile X site, nor its relationship to the gene responsible for the clinical expression of the syndrome is understood. However, based upon genetic linkage studies, as well as in situ hybridizations, the fragile X site and its associated gene are tightly linked if not coincident.

The present application provides a new procedure for detecting the fragile X site at the molecular level. It provides a molecular method for the diagnosis of the fragile X syndrome, describes a unique open reading sequence at the suspected gene locus and provides probes to the fragile X region.

SUMMARY OF THE INVENTION

An object of the present invention is a method for diagnosing fragile X syndrome.

A further object of the present invention is the provision of a sequence of the FMR-1 gene.

An additional object of the present invention is a method of detecting the fragile X syndrome by measuring the mRNA or protein from the FMR-1 gene.

Another object of the present invention is a method of detecting the fragile X syndrome by measuring CGG repeats.

A further object of the present invention is a method of detecting the fragile X syndrome by measuring the methylation associated with a CpG island.

Thus in accomplishing the foregoing objects there is provided in accordance with one aspect of the present invention as a composition of matter, a 3.8 kb cDNA clone containing the FMR-1 gene. A further aspect is a 5222 bp genomic DNA sequence containing at least a fraction of the FMR-1 gene.

A further embodiment of the present invention is a group of cosmid probes for the selection of the FMR-1 gene in the fragile X syndrome.

An additional embodiment of the present invention is a method of detecting fragile X syndrome comprising the steps of digesting DNA from an individual to be tested with a restriction endonuclease and detecting the restriction fragment length polymorphism with hybridization to probes within the fragile X locus and southern blot analysis. In a preferred embodiment of the present invention, the probe is pE5.1 and the restriction endonucleases are selected from the group consisting of EcoR I, Pst I, Xho I and BssH II.

Alternate embodiments of the present invention include detecting the fragile X syndrome by measuring the expression of the FMR-1 gene either as the amount of mRNA expressed or as the amount of FMR-1 protein produced. Another embodiment of the present invention includes a method of detecting X-linked disease comprising the steps of detecting variation in the $(CGG)_n$ repeat at the 5' end of the FMR-1 gene by measuring the length of the repeat, wherein n for normal ranges between 16 and 30 and n for X-linked disease is greater than 30. A variety of methods are available to detect the dosage measurements of the repeat. These procedures can be selected from the group consisting of visual examination, densitometry measurement, quantitative radioactivity and quantitative fluorescence as well as pulsed field gel electrophoresis and fluorescence in situ hybridization.

Other and further objects, features and advantages will be apparent and eventually more readily understood from a reading of the following specification and by reference to the accompanying drawings forming a part thereof, wherein examples of the presently preferred embodiments of the invention are given for the purpose of the disclosure.

DESCRIPTION OF THE DRAWINGS

FIG. 11 is a sequence (SEQ ID NO: 24) of the 1 kb PstI DNA fragment containing the CpG island and "CGG" repeat. The differences between this sequence and that reported by Kremer et. al. *Science* 252:1711–1714 (1991) are shown in lower case letters. The name of restriction sites are shown above their recognition sequences. The locations of PCR primers are shown by solid line below. The sequence has been corrected for the FMR-1 at the positions 384–385 (CG vs GC) Verkerk et. al. *Cell* 65:905–914 (1991). Primer a (SEQ ID NO: 15), Primer b (SEQ ID NO: 16), Primer c (SEQ ID NO: 10), Primer d (SEQ ID NO: 17), Primer e (SEQ ID NO: 18), Primer f (SEQ ID NO: 11), Primer g (SEQ ID NO: 19) and Primer h (SEQ ID NO: 20).

Figure 1:
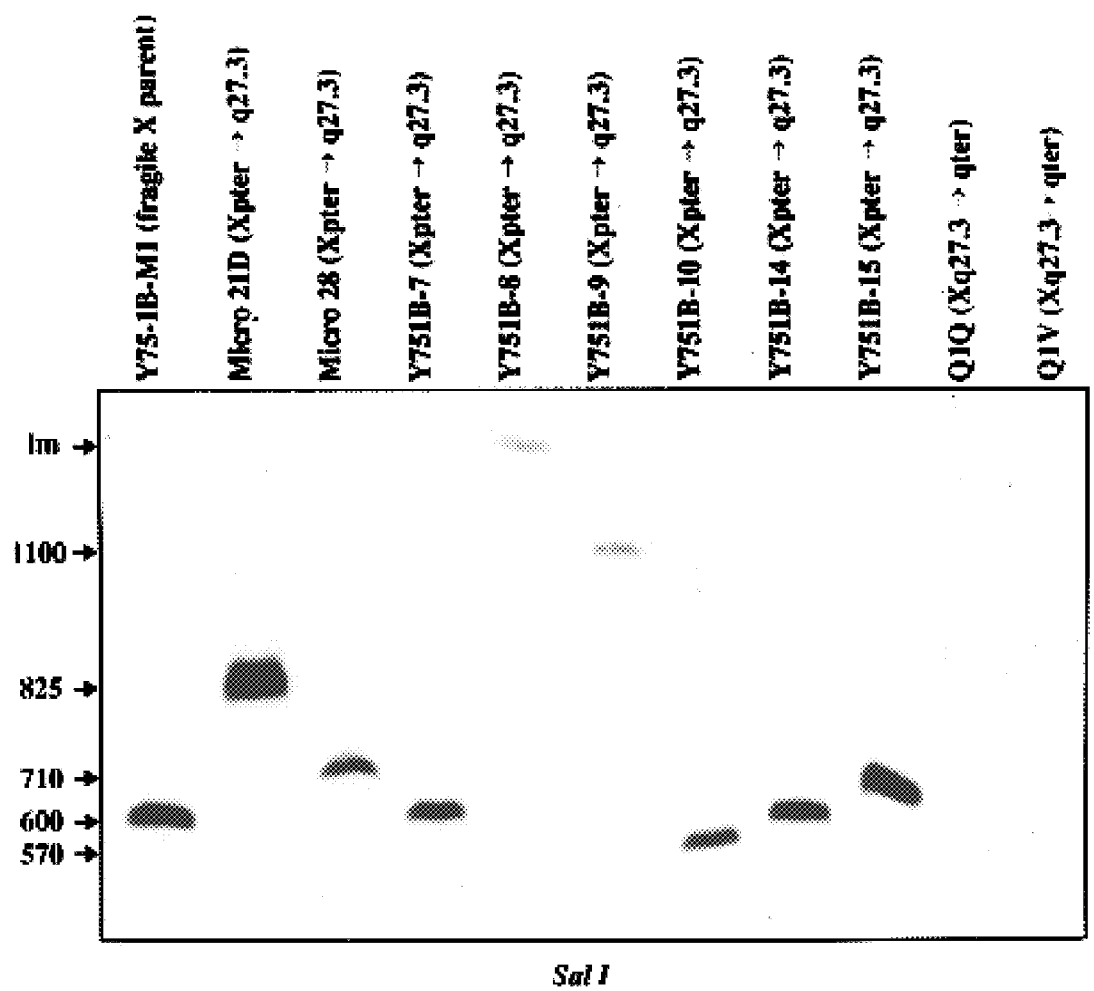
FIG. 1 is a Southern blot analysis of pulsed field gel resolved Sal I digested DNA of proximal translocation hybrids probed with p46-1.1.

The drawings and figures are not necessarily to scale and certain features mentioned may be exaggerated in scale or shown in schematic form in the interest of clarity and conciseness.

DETAILED DESCRIPTION OF THE INVENTION

It will be readily apparent to one skilled in the art that variations, substitutions and modifications may be made to the invention disclosed herein without departing from the scope and the spirit of the invention.

Each sample to be tested herein for the fragile X site is derived from genomic DNA, mRNA or protein. The source of the genomic DNA to be tested can be any medical specimen which contains DNA. Some examples of medical specimen include blood, semen, vaginal swabs, buccal mouthwash, tissue, hair and mixture of body fluids. As used herein the term "polymerase chain reaction" or "PCR" refers to the PCR procedure described in the patents to Mullis, et al., U.S. Pat. Nos. 4,683,195 and 4,683,202. The procedure basically involves: (1) treating extracted DNA to form single-stranded complementary strands; (2) adding a pair of oligonucleotide primers, wherein one primer of the pair is substantially complementary to part of the sequence in the sense strand and the other primer of each pair is substantially complementary to a different part of the same sequence in the complementary antisense strand; (3) annealing the paired primers to the complementary sequence; (4) simultaneously extending the annealed primers from a 3' terminus of each primer to synthesize an extension product complementary to the strands annealed to each primer wherein said extension products after separation from the complement serve as templates for the synthesis of an extension product for the other primer of each pair; (5) separating said extension products from said templates to produce single-stranded molecules; and (6) amplifying said single-stranded molecules by repeating at least once said annealing, extending and separating steps.

As used herein fluorescence in situ hybridization or "FISH" refers to the procedure described in Wotta, et al., Am. J. of Human Genetics, 46, 95–106 (1988) and Kievits, et al., Cytogenet. Cell Genet., 53134–136 (1990). The procedure basically involves the steps of preparing interphase or metaphase spreads from cells of peripheral blood lymphocytes and hybridizing labeled probes to the interphase or metaphase spreads. Using probes with mixed labels allows visualization of space, order and distance between hybridization sites. After hybridization the labels are examined to determine the order and distance between the hybridization sites.

As used herein, the term "pulsed field gel electrophoresis" or "PFGE" refers to a procedure described by Schwartz, et al., Cold Springs Harbor Symposium, Quantitative Biology, 47:189–195 (1982). The procedure basically comprises running a standard electrophoresis gel (agarose, polyacrylamide or other gel known to those skilled in the art) under pulsing conditions. One skilled in the art recognizes that the strength of the field as well the direction of the field is pulsed and rotated in order to separate megabase DNA molecules. Current commercial systems are computer controlled and select the strength, direction and time of pulse depending on the molecular weight of DNA to be separated.

One embodiment of the present invention as a composition of matter is a 3.8 kb cDNA clone (SEQ ID NO: 1) containing the FMR-1 gene.

Another embodiment of the present invention is a 5222 bp genomic DNA (SEQ ID NO: 23). This DNA includes a 4188 bp (SEQ ID NO: 2) sequence from the distal Eco RI site containing the fragile X region and a 229 bp genomic DNA (SEQ ID NO: 3) from the proximal Eco RI site.

One embodiment of the present invention is a method of detecting Fragile X syndrome comprising the steps of digesting DNA from an individual to be tested with a restriction endonuclease and detecting the restriction fragment length to polymorphism (RFLP) with hybridization to probes within the fragile X locus and southern blot analysis. One skilled in the art will readily recognize that a variety of restriction endonucleases can be used. In the preferred embodiment the restriction endonuclease is selected from the group consisting of EcoR I, Pst I, Xho I and BssH II.

In the method of detection, it is found that the probe pE 5.1 is used in the preferred embodiment. One skilled in the art readily recognizes that other probes consisting of some sub fraction (i.e., a fragment) of the full probe pE5.1 will hybridize to the unique fragment lengths and thus can be used.

An alternative method for detecting the Fragile X syndrome comprises the step of measuring the expression of the FMR-1 gene. The FMR-1 gene can be measured by either measuring the amount of mRNA expressed or by measuring the amount of FMR-1 protein.

When measuring the amount of mRNA expressed, the amount of mRNA is determined by the steps of extracting RNA from any tissue source including fibroblast and lymphoblastoid cell lines of the individuals to be tested. From the RNA of FMR-1, a cDNA is prepared. From RNA of a control gene a cDNA is prepared. Then quantification is achieved by comparing the amount of mRNA from FMR-1 with the mRNA from the controlled gene. In the preferred embodiment, the quantification step includes PCR analysis of the FMR-1 cDNA and PCR analysis of the control gene cDNA. The PCR products are electrophoresed and ethidium bromide stained. The products are then quantified by comparing the FMR-1 product versus the control gene product after the ethidium bromide staining. The oligonucleotide primers for the fragile X site are SEQ ID NO: 8 and SEQ ID NO: 9. One example of the control gene is HPRT and the oligonucleotides are SEQ ID NO: 12 and SEQ ID NO: 13.

When measuring the amount of FMR-1 protein produced, one can use any of the variety of methods known in the art to detect proteins, including monoclonal antibodies, polyclonal antibodies and protein assays. In the preferred embodiment, the antibodies detect SEQ ID NO: 14.

The methods described herein can also be used to detect X-linked disease. The method comprises the steps of detecting variation of the $(CGG)_n$ repeat found at the 5' end of the FMR-1 gene by measuring the length of the repeat wherein n (number of repeats) for normal is in the range between 16 and 30 and n for X-linked diseases is in the range of greater than 30. In the case of Fragile X, n is usually at least twice the range of normal. Types of disease which can be detected are X-linked mental retardation both of fragile X and non-fragile X type, X linked manic depressive disease, TKCR syndrome and Martin-Bell syndrome.

The method of dosage compensation by measuring the amount or length of the repeat can be done by using FISH. In the FISH method, the repetitive sequence can be used as a probe to distinguish between normal and fragile X syndrome simply by the presence or absence of a signal to the repetitive sequence. In this case, the application of the repeat sequence provides a sufficiently large target for the hybridization. Thus, it is possible that very sensitive FISH might detect transmitting males (with 50–100 copies of the CGG) even though these would be lost to routine microscopy and detection. Although FISH is usually applied to metaphase nuclei, in the present invention it is applicable to both metaphase and interphase for the detection of X-linked disease.

Alternate methods to measure the dosage measurement of the repeat can include visual examination, densitometry measurement, quantitative radioactivity and quantitative fluorescence.

In one embodiment the size of the repeat is determined by dosage measurements of Southern blotting analysis of restriction enzyme digests with probes contained within the FMR-1 gene region.

It is also known that the method of PFGE can be used to detect variation at the fragile X locus.

In another embodiment the variation of the (CGG)n repeat is measured by PCR. A variety of PCR primer pairs can be used including SEQ ID NOS: 19 and 11 or SEQ ID NOS: 15 and 11 or SEQ ID NOS: 10 and 11. In this method the preferred oligonucleotide primer pair is SEQ ID NO: 10 and SEQ ID NO: 11.

Figure 4:
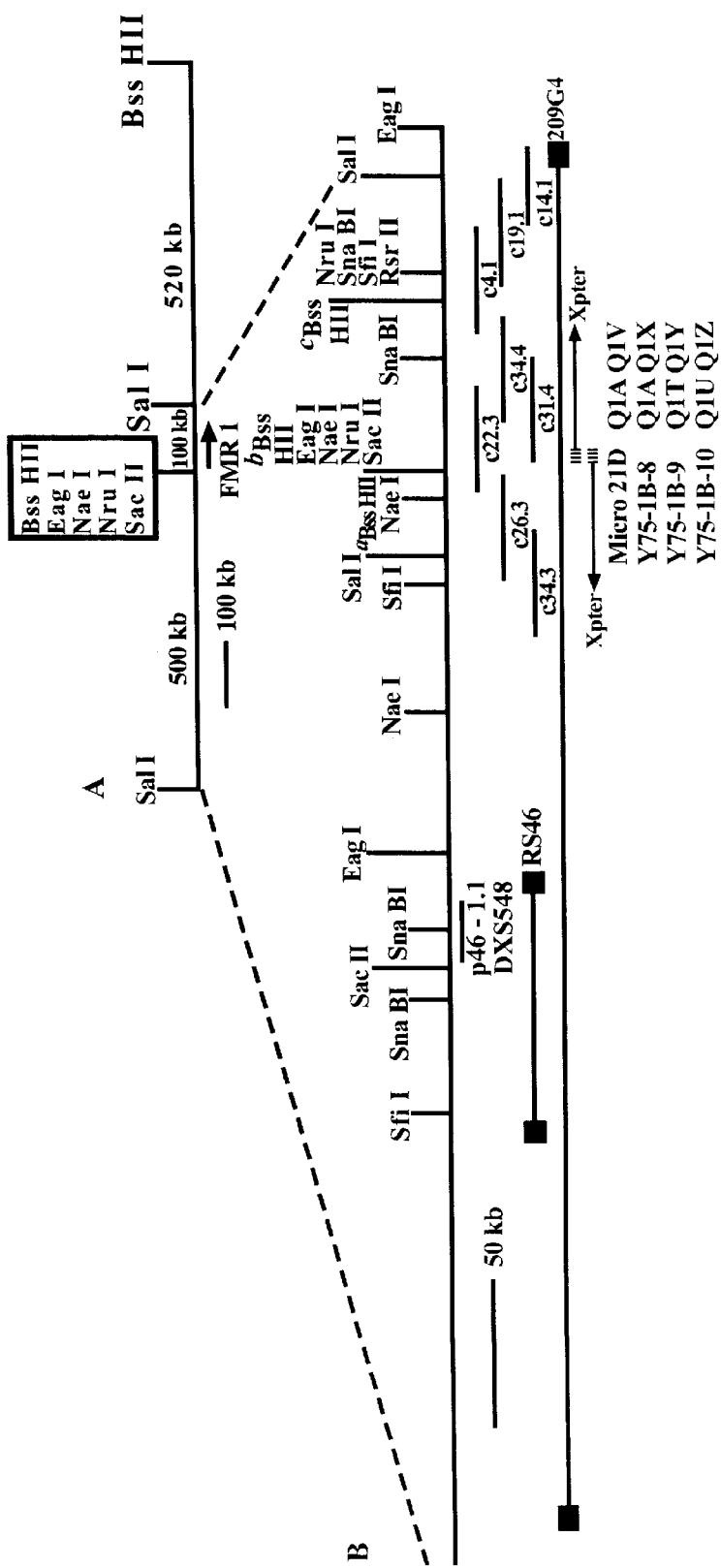
FIG. 4 is a physical map of the fragile X region of a genomic and YAC 209G4 DNA.

Another embodiment of the present invention is the cosmid probes shown in FIG. 4. These cosmid probes can be selected from the group consisting of C 22.3, C 34.4, C 31.4, C 4.1, C 34.3, C 26.3 C 19.1 and C14.1. These cosmid clones are Sau 3A digests of the YAC 209G4. These digests were cloned into p2CpG. This results in inserts from 35–45 Kb. The ends are defined by their positions on the map of FIG. 4. These cosmid probes overlap the range in which the FMR-1 gene is located.

In detecting the fragile X sites the length of CA polymorphisms at the fragile X site can be measured by performing a PCR assay and measuring the length of the amplified products. In the PCR assay, the oligonucleotide primers are SEQ ID NO: 6 and SEQ ID NO: 7.

Another method of detecting X linked mental retardation (fragile X syndrome) is to measure the methylation associated with a CpG island in the fragile X area, wherein a methylation-sensitive restriction endonuclease is used to digest the extracted DNA to be tested and then the digested DNA is amplified. If products are amplified in males it indicates the presence of methylation and the fragile X gene defect. In this procedure a variett of restriction endonuclease can be used including BssH II, Eag I, Sac II, Hpa II and Msp I. The oligonucleotide primer pairs are selected from the group consisting of SEQ ID NOS: 19 and 20, SEQ ID NOS: 19 and 11, SEQ ID NOS: 19 and 17 and SEQ ID NOS: 19 and 16. Additionally, restriction endonuclease Nhe I and Xha I can be used with primer pair SEQ ID NOS: 19 and 11 or SEQ ID NOS: 15 and 11 or SEQ ID NOS: 10 and 11. The restriction endonucleaseNhe I can be used with primer pair SEQ ID NOS: 18 and 11. In the preferred embodiment the restriction endonuclease is BssH II and the primer pair is SEQ ID NOS: 19 and 20.

The following examples are offered by way of illustration and are not intended to limit the invention in any manner. In the examples all percentages are by weight, if for solids and by volumes, if for liquids and all temperatures are in degrees Celsius unless otherwise noted.

EXAMPLE 1

Pulsed Field Gel Electrophoresis Southern blot analysis of genomic DNA or YAC DNA resolved by PFGE was performed essentially as described (Smith, et al., Pulsed-field gel electrophoresis and the technology of large DNA molecules. In Genome Analysis: A Practical Approach; Oxford:IRB Press, pp.41–72, 1988). In this procedure, trypsinized and washed mammalian cells were suspended in molten agarose (final concentration 0.5% wt/vol; Baker) prepared in SE buffer (75 mM NaCL, 25 mM EDTA, pH 8.0) at a final concentration of $1.5 \times 10^7$ cells/mi. Chromosomal DNAs were isolated from YAC clones. Yeast cells from a 10 ml saturated culture were harvested, rinsed once in 50 mM EDTA, pH 8.0 and recovered in 0.5 ml SBE-zymolase (1 M sorbitol, 25 mM EDTA pH 8.0, 14 mM 2-mercaptoethanol, 1 mg/ml zymolase [ICN]). 0.5 ml 1% Seaplaque agarose (FMC) in SBE (without zymolase) was added and the suspension transferred to plug molds. Spheroplast generation (for yeast cells) was for 5 hours to overnight in SBE-zymolase. Cell lysis (mammalian or yeast cells) was for 2 days in ESP (0.5 M EDTA, pH 9.5, 1% N-laurolsarcosine, 1 mg/ml proteinase K) at 50° C. Restriction endonuclease digestion was performed using the manufacturer's recommended buffers and conditions with a 50 µl plug slice in 250 µl of buffer containing 50 units of enzyme. For double digests, the plugs were rinsed and equilibrated, following digestion with the first enzyme, with the second buffer several times prior to digestion with the second enzyme. PFGE was carried out on a Bio-Rad Contour-Clamped Homogeneous Electric Field (CHEF) DRII apparatus through 1% agarose (BRL) at 200 V and 14° C. in 0.5× TBE buffer (45 mM Tris-borate, 1 mM EDTA). For resolution of fragments of ≈200–1200 kb, switch time was 60 sec for 17 hrs followed by 90 sec for 10 hrs; for resolution of fragments ≈10–500 kb, the switch times were ramped from 5 sec to 50 sec over 27 hrs. Southern blotting and hybridization were carried out as described in the art with the exception that acid depurination in 0.25 M HCl was allowed to proceed 20 min for pulsed-field gels. Radiolabeled probes were synthesized by random priming from 50 ng gel purified fragments except when intact cosmids were used which were nick translated (Boehringer Mannheim kit; following manufacturer's recommendations). For genomic probes containing repetitive elements, repeat suppression was accomplished by preassociation with 1–3 mg of sonicated human placental DNA in 100–300 µl of 5× SSC (1× SSC is 150 mM NaCl, 15 mM NaCitrate, pH 7.0) for 3–10 min at 65° C. prior to the addition to the filter. Washing was carried out to a final stringency wash of 0.2× SSC for 15 min at 65° C. prior to autoradiography. *S. cerevisiae* strain YNN295 chromosomes (BioRad), concatamers of phage lambda (BioRad) or high molecular weight markers (BRL) were used as size standards.

EXAMPLE 2
PCR Analysis of DXS548 Alleles

Amplification was carried out on 0.2–0.5 µg of genomic DNA in a 10 µl total reaction containing 0.25 mM dNTPs, 40 ng of primers SEQ. ID. NO. 6 and SEQ. ID. No. 7, and 0.25 units of Taq polymerase in a buffer of 10 mM Tris-HCl, 50 mM KCl, 12 mM MgCl and 0.01% gelatin. Twenty three cycles of PCR were carried out in the following fashion; 3 cycles of 1 min each at 97° C., 62° C. annealing and 72° C. extension followed by 20 additional cycles with the annealing temperature lowered to 55° C. The reaction volume was then increased to 50 µl with the same reaction components and concentrations except that one primer was 5' end-labelled with $Y^{32}$P-ATP. PCR was continued for 10 cycles of 1 min each at 95° C. denaturation, 62° C. annealing and 72° C. extension. PCR products were analyzed by electrophoresis of 2 µl of reaction through a 40 cm 6% polyacrylamide denaturing sequencing gel for approximately 2.25 hrs. The gel was dried without fixing and exposed to X-ray film overnight at room temperature.

EXAMPLE 3
Cosmid Library Construction of YAC 209G4

Agarose plugs (0.5% SeaPlaque FMC) containing 5–10 µg of yeast DNA were prepared. 100 µl blocks of DNA were equilibrated on ice in 0.5 ml of Mbo I digestion buffer, containing 0.1 mg/ml bovine serum albumin (BSA, MB grade; Boehringer Mannheim). After 2–3 hrs, the buffer was replaced by 150 µl of fresh buffer to which Mbo I was added (0.0001–0.0007 units). Following overnight incubation on ice, digestion was carried out for 40 min at 37° C. The agarose blocks were melted, the DNA dephosphorylated with 1 unit calf intestinal alkaline phosphatase (Beohringer Mannheim), and treated with 2.5 units of agarase (Calbiochem). The solution was extracted twice with phenol/chloroform, once with chloroform, the DNA precipitated with ethanol and dissolved in 10 mM Tris, 0.1 mM EDTA (pH 7.4) at a concentration of 500 ng/µl. 250 ng of DNA was ligated to 500 ng of Bst Bl (dephosphorylated) and Bam HI digested vector (p2CpG). Ligation and packaging was carried out according to standard procedures. Cosmids containing human inserts were selected by hybridizing with human specific Alu-repeat probe. These cosmids can be seen in FIG. 4.

EXAMPLE 4
YAC and Cosmid Subcloning

YACs were subcloned following isolation of the intact chromosome by preparative PFGE and EcoR I digestion of the DNA in molten agarose (Seaplaque; FMC). Fragments were phenol/chloroform extracted, ethanol precipitated, recovered and ligated into EcoR I cut, dephosphorylated, lambda ZAP II arms according to manufacturer's recommendations (Stratagene). Cosmids were subcloned following an alkaline lysis isolation and EcoR I digestion. Fragments were phenol/chloroform extracted and ethanol precipitated prior to ligation into lambda ZAP II arms as with YAC fragments. In the case of both cosmids and YACs, 75 ng EcoR I fragments were ligated to 1 ug vector arms. Selected phage were converted into pBluescript II SK-clones following in vivo excision of plasmid with insert according to manufacturer's guidelines.

EXAMPLE 5
cDNA Library Screening

A human fetal brain lambda gt11 cDNA library (Clonetech, Palo Alto, Calif.) of $1.3 \times 10^6$ independent clones with insert lengths of 0.7–4.0 kb was used. The library was plated on 15 cm plates at a density of 50,000 pfu per dish using strain LE392. Filter lifts were prepared according to standard techniques and the library screened with cosmid DNA hexanucleotide labelled with $^{32}$P-dATP and $^{32}$P-dCTP. The labelled DNA was first prehybridized with 100 µg of total sheared human genomic DNA and 100 µg cosmid vector DNA in 5× SSC at 65° C. for 2 hrs. Following hybridization for 16 hrs, the filters were washed to a stringency of 0.1× SSC. The filters were exposed to Fuji film with intensifying screens for 2 days at −80° C.

EXAMPLE 6
Fluorescent In Situ Hybridization

In situ hybridizations of total YAC-containing yeast DNA and cosmids were performed. Fragile X expression was induced by 96 hr culturing of lymphocytes (PHA stimulated from a male fragile X patient) in medium TC199 (Gibco) supplemented with 10% bovine fetal calf serum and, for the last 24 hrs, 10 µg/ml methotrexate (Lederle). Chromosomes were prepared on slides using standard techniques.

Slides were washed with PBS and incubated for 1 hr at 37° C. in RNase A (100 µg/ml) in 2× SSC. The slides were then incubated 10 min with pepsin (Serva; 0.1 mg/ml in 0.01 N HCL), fixed in 1% (vol/vol in PBS, 50 mM $MgCl_2$) formaldehyde (Merck) and dehydrated in cold ethanol. Biotinylated total yeast and cosmid DNA were preannealed for 1–4 hrs in the presence of sonicated human genomic DNA and hybridized to the chromosomes overnight using 150 ng (yeast) or 40 ng (cosmid) of probe in 10 µl of 50% formamide, 2× SSC, 10% dextran sulfate under an 18 mm$^2$ coverslip sealed with rubber cement. In some experiments, 2 ng/µl pBamX5, a human repetitive sequence detecting the pericentromeric region of the human X, was separately denatured and added to the hybridization solution.

The signals were amplified by two layers of avidin-FITC (Vector) and one layer of biotinylated goat anti-avidin (Vector). The slides were then washed with PBS and mounted in antifade medium of 2% DABCO in glycerol containing propidium iodide (0.03 µg/ml). Microscopic analysis was performed with a Leitz Aristoplan microscope with FITC (K3 block) and DAPI (A block) detection. Photographs were made using Ektachrome 400 (Kodak) daylight slide film.

EXAMPLE 7
Northern Blot Analysis

Total RNA was extracted using guanidinium isothiocyanate followed by centrifugation through cesium chloride. Poly(A)$^+$ RNA was selected by passage through oligo(dT) cellulose. Human brain, liver, and fetal poly(A) RNA was purchased from Clontech Laboratories (Palo Alto, Calif.).

Five μg of poly(A) containing RNA or 25 μg of total RNA were precipitated and dissolved in 20 μl of 50% (vol/vol) formaldehyde and 1× MEN (20 mM MOPS, pH 6.8, 5 mM sodium acetate, 1 mM EDTA) and incubated for 10 min at 60° C.; 5 μl of dye marker (50% sucrose, 0.5% bromophenolblue) was added and the samples were loaded on a formaldehyde-agarose gel. Electrophoresis was carried out for 3 hrs. at 100 V and the gel then soaked for 30 min in 20× SSC and blotted onto a nitrocellulose or nylon (GeneScreen Plus, Dupont) overnight in 10× SSC (Thomas, 1980). The RNA was fixed to the membranes by baking under vacuum for 2 hrs at 80° C. The membranes were prehybridized in 50% formamide, 5× Denhart's, 50 mM sodium phosphate, pH 6.8, 10% dextran sulfate and 100 μg of denatured salmon sperm DNA at 42° C. for 2–4 hrs. Hybridization with the probe was for 16–20 hrs at 42° C. in the above buffer. Filters were washed with 3× SSC, 0.1% SDS at 50° C. and then the SSC concentration was lowered according to the level of background, with a final wash in 0.1× SSC, 0.1% SDS.

EXAMPLE 8
RT-PCR Quantitation of the FMR-1 Transcript

A PCR based test is devised in which the transcription product from the FMR-1 gene is quantitated with respect to an internal control (HPRT gene), in RNA samples from Fragile X and normal cell lines. In this method the total RNA was extracted from lymphoblastoid cell lines derived from Fragile X affected individuals and normal controls. The cDNA synthesis was performed in vitro from 5 μg of total RNA using oligo-dT and random primers via a reverse transcriptase reaction. Then PCR from single stranded cDNA was carried out using primers specific for the HPRT cCNA (SEQ ID NOS: 12 and 13) and primers specific for the FMR-1 cDNA (SEQ ID NOS: 8 and 9). The PCR conditions were as follows: 94° C., 1 min; 55° C. 1 min; 72° C. 1 min 45 sec; for 28 cycles and 7 min final extension at 72° C. The PCR products were run on an ABI Horizontal Electrophoresis device, by which the ethidium bromide stained products of each gene were exactly quantitated with respect to each other. Quantitative variations in the expression of the FMR-1 gene in Fragile X patients derived cell lines was then monitored.

EXAMPLE 9
Isolation of YACs Spanning the Fragile X Translocation Breakpoints

Through regional mapping of YAC clones containing DNA inserts derived from the distal human Xq, an 80 kb YAC (RS46) was found to map within Xq27.3 proximal to the fragile X-associated hybrid breakpoints. A 4.0 kb subclone (p46-1.1) of RS46 identified a normal 600 kb Sal I fragment on PFGE that was altered in size in 6 of 8 proximal translocation hybrids (FIG. 1). In FIG. 1, Y75-1B-M1 is a somatic cell hybrid containing the intact fragile X chromosome from which all other hybrids were derived. Lanes 2–9 are proximal translocation hybrids containing centric human Xpter-q27.3 translocated to different rodent chromosome arms. Q1Q and Q1V are distal translocation hybrids containing human Xq27.3-qter translocated to different centric rodent chromosome. The distal translocation hybrids have lost the human sequence detected by p46-1.1. Hybrids Y751B-7 and Y751B-14 show the same 600 kb Sal I fragment as the parental hybrid, however all other proximal translocation hybrids show variant bands indicating that probe p46-1.1 detects a sequence within 600 kb of these translocation breakpoints.

PFGE analyses of these hybrids, with more distant X-linked probes, showed identical band sizes and therefore similar methylation patterns as might be expected since the hybrids were all derived from the same parental fragile X somatic cell hybrid (Y75-1B-M1). These data suggest that in 75% of the proximal translocation hybrids, the human breakpoint is within the 600 kb Sal I fragment observed in the parental, intact fragile X hybrid. In the translocation hybrids, the distal human Sal I site is lost and replaced by heterologous translocations containing different rodent Sal I sites.

Figure 2:
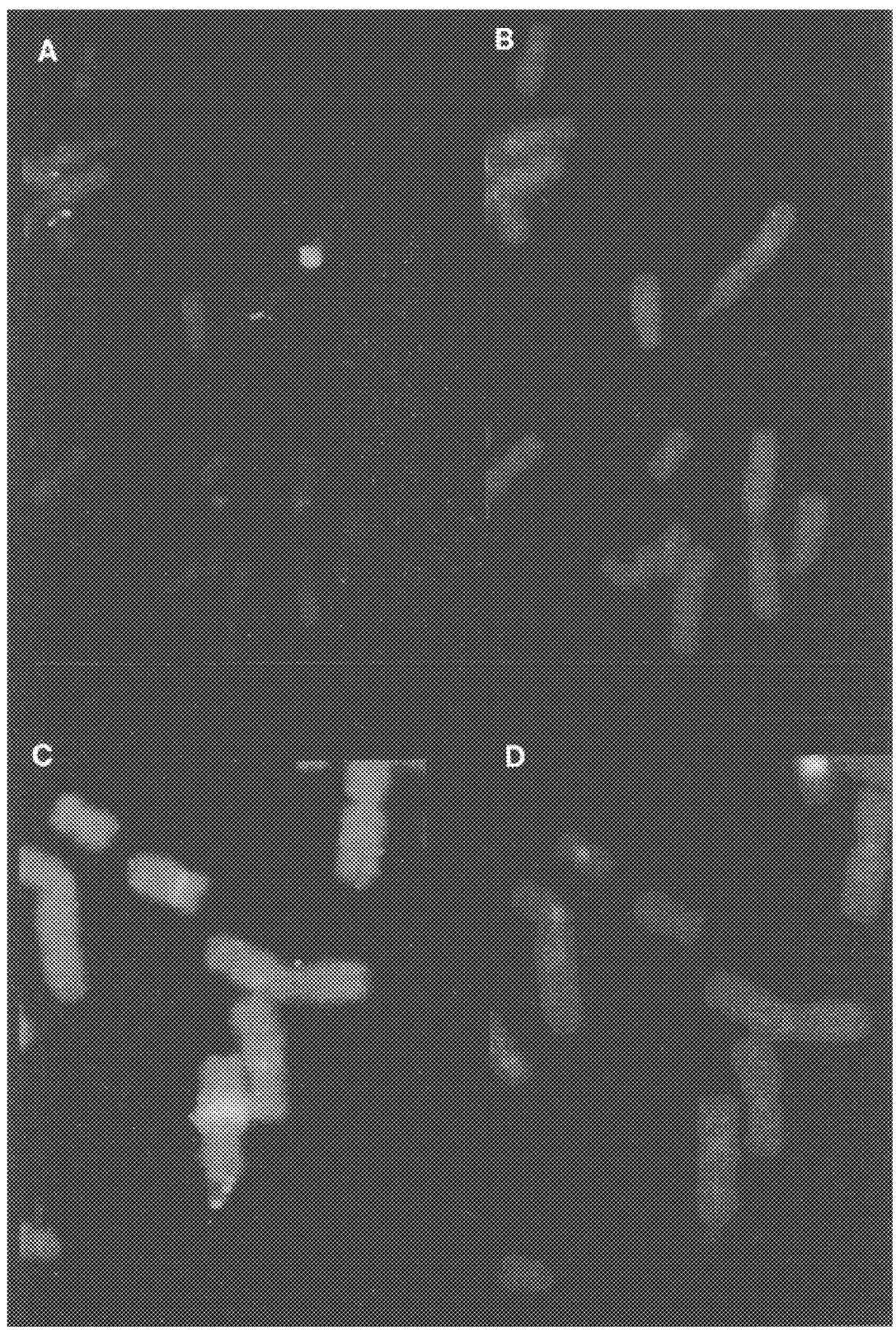
FIGS. 2A–2D are show fluorescent in situ hybridization of YAC 209G4 and cosmids to the fragile X site at Xq 27.3 of an affected male patient.

Since YAC RS46 does not hybridize to the DNA of the distal translocation hybrids and therefore does not cross these translocation breakpoints, additional YACs were sought of this region. A YAC library developed at the Human Polymorphism Study Center (CEPH) was screened using RS46 specific oligonucleotide primers SEQ ID NOS: 4 and 5 or SEQ ID NOS: 6 and 7. A YAC of 475 kb (209G4) was identified which completely overlaps YAC RS46 and includes sequences distal to the proximal translocation breakpoints which are present in 13 or 14 distal translocation breakpoints. YAC 209G4 encompasses 86% (19/22) of both the proximal and distal translocation breakpoints and thus identifies a fragile X-associated breakpoint cluster region. In situ hybridization using YAC 209G4 showed localization to the expressed fragile X site (FIG. 2). In FIG. 2, panel A represents the localization of YAC 209G4 to the expressed fragile X site. The centrometric signal is due to pBamX5, indicating the human X chromosome with slight hybridization to acrocentric chromosomes; Panel B shows a DAPI stained spread of panel A showing the expressed fragile X site; Panel C shows localization of cosmid 7.1 to the fragile X region; and finally, panel D shows localization of cosmid 22.3 to the fragile X region.

The signal includes both flanking boundaries of the isochromatid gap of the fragile site as well as the gap itself, suggesting the presence of uncondensed DNA within the fragile site and indicating that YAC 209G4 includes this region.

Figure 3:
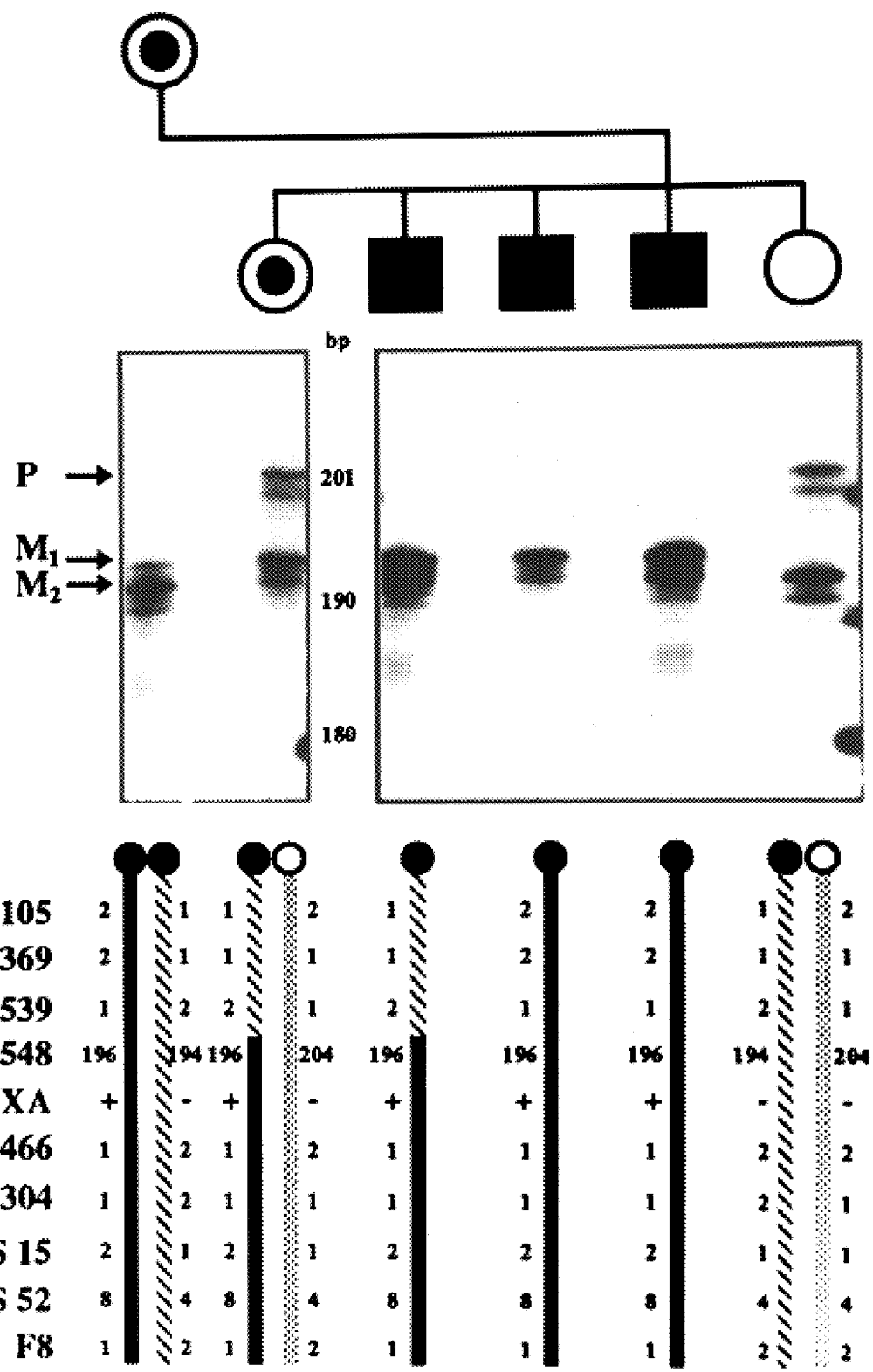
FIG. 3 is a PCR analysis of DXS548 alleles in a fragile X family with recombinant individuals.

The close proximity of these YACs to the fragile X locus was independently supported by genetic linkage studies between a polymorphism identified in YAC RS46 and the fragile X locus. DXS548 is a dinucleotide repeat which reveals 9 alleles of variable length that are informative in >80% of fragile X families. In highly selected families previously shown to have crossovers with tightly linked flanking markers, DXS548 cosegregated, without recombination, with the fragile X locus (lod score of 6.95 at Θ=0). As shown in FIG. 3, a carrier daughter and affected son are recombinant between the fragile X locus (FRAXA) and proximal markers DXS 539 (probe JH89) and DXS 369 (probe RN1) which map approximately 5 cM proximal to FRAXA with lod scores >40. The carrier mother shows two DXS 548 alleles at 196 and 194 bp (M1 and M2, respectively). The paternal 204 allele of the father is seen in the carrier daughter (II-1) who also inherited the maternal 196 bp allele. All three affected males inherited the 196 bp maternal allele (compare with the 194 allele of the normal daughter (II-5). The carrier daughter (II-1) and affected son (II-2) are both recombinants between proximal markers DXS 150, DXS 369 and DXS 539. However, these individuals are non-recombinant with DXS 548, placing this locus to the crossovers closer to the fragile X locus. Therefore, DXS 548 positions YACs RS46 and 209G4 near the mutation responsible for the clinical phenotype of the fragile X syndrome.

EXAMPLE 10

Physical Map of YAC 209 G4

A physical map of YAC 209G4 and of the corresponding genomic region was developed and is shown in FIG. 4. In FIG. 4(A), the physical map of the fragile X chromosome in the vicinity of the Fragile X locus is shown. The Sal I sites which give rise to the 600 kb fragment seen in hybrid Y75-1B-M1 probed with p46-1.1 and the normal 620 kg BssH II fragment observed in normal X chromosomes can be seen. The sites within the box are those previously shown to be methylated on the fragile X chromosome. The position and orientation of FMR-1 is shown.

In FIG. 4(B), a higher resolution physical map derived from both YAC inserts and genomic DNA is shown. Probe p46-1.1 and the DXS 548 loci are shown as are the positions of cDNAs and cosmids. YACs RS46 and 209G4 are shown below in alignment with the map (Hatched boxes indicate YAC vector sequences). The positions of the translocation breakpoints are shown as well as the orientation of the map relative to the X chromosome telomeres.

A CpG-island containing 5 infrequent-cleaving restriction endonuclease sites was identified 150 kb distal to CSX 548. This CpG-island appears hypermethylated on the fragile X chromosome. It is known in the art that there is an absence of a normal 620 kb BssH II fragment (FIG. 4A) in patients and most carriers of the fragile X syndrome. The absence of the fragment appears to be due to the methylation (and therefore resistance to cleavage) of the BssH II site (b in FIG. 4B) leading to a very large band which fails to resolve on PFGE. Since CpG-islands often are found 5' to mammalian genes and since methylation of such islands may influence expression of associated genes, it is possible a gene may reside nearby this fragile X-related CpG-island and its expression (or lack of) may be responsible for at least a portion of the fragile X phenotype.

EXAMPLE 11

Cosmid Contig Surrounding the Fragile X-Related CpG Island and Breakpoint Cluster Region To characterize the region surrounding the CpG-island, a cosmid library was constructed from the yeast clone harboring YAC 209G4 and cosmids containing human DNA were identified by hybridization to human-specific repetitive elements. In situ hybridization with several human cosmids showed signals in (FIG. 2C) and on the edge (FIG. 2D) of the fragile X gap. A four cosmid contig was identified which spans the fragile X-related CpG island (FIG. 4B) from BssH II site a (cosmid 22.3) through BssH II site c (cosmid 4.1).

Figure 5:
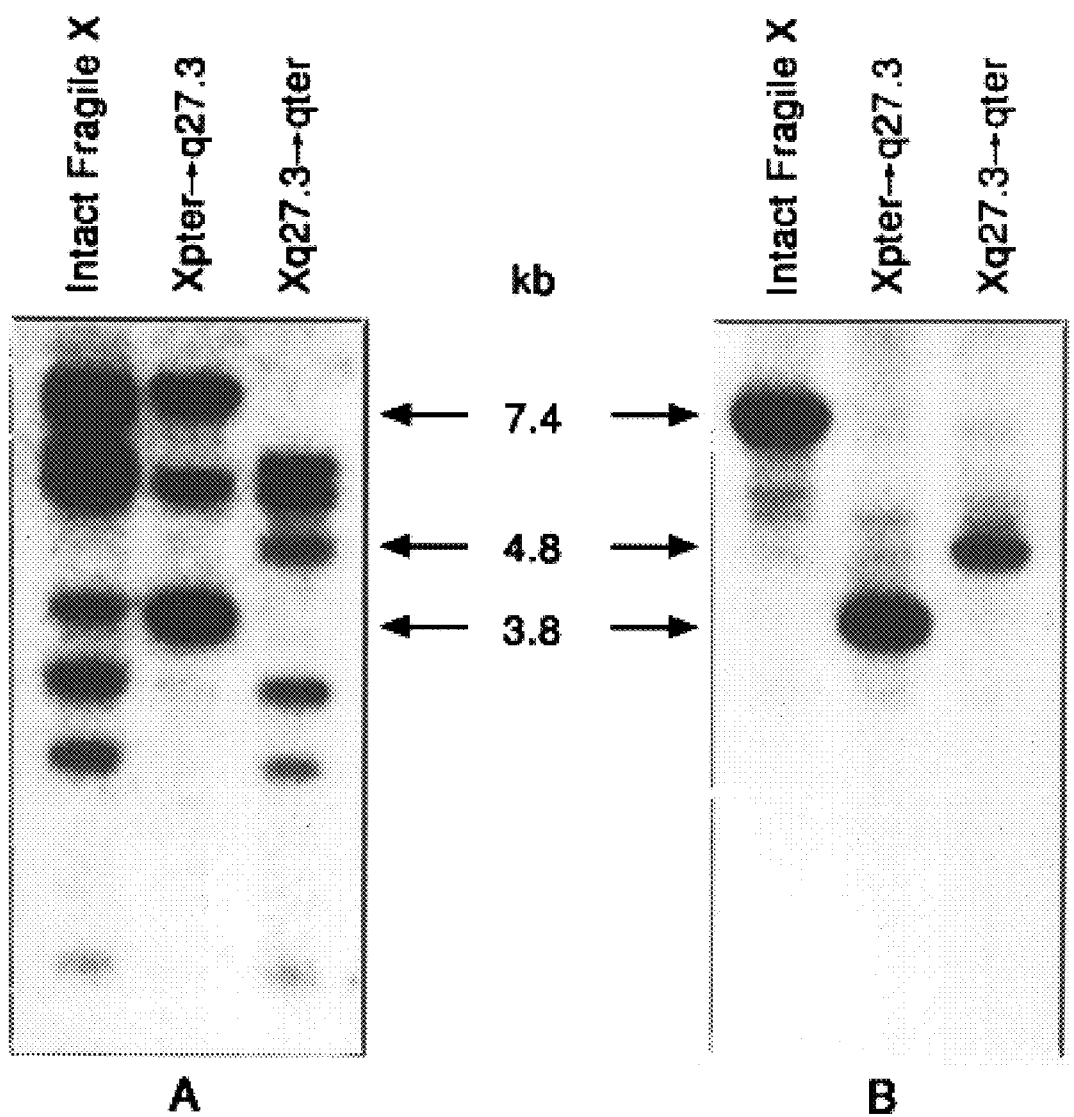
FIGS. 5A and 5B depict a Southern blot analysis of fragile X associated translocation breakpoints. In (A) the Southern blot is hybridized with cosmid 22.3 and in (B) the same filter is hybridized with pE5.1.

Cosmid 22.3 was found to include the breakpoints of 11 of 16 tested translocation hybrids (4/5 proximal translocations and 7/11 distal translocations; all 16 breakpoints map within YAC 209G4). As shown in FIG. 5A, nine bands (including doublet bands at 5.6 and 5.5 kb), surveying approximately 44 kb of genomic DNA, are observed on Southern analysis of EcoR I digested DNA of the intact fragile X hybrid (Y75-1B-M1) following hybridization with radiolabeled and preannealed cosmid 22.3. Of these nine bands, three are present in the distal Q1X (with a novel 4.8 kb junctional fragment). The 7.4 kb band of the intact X hybrid Y75-1B-M1 is absent in both translocation hybrids indicating that both breakpoints fall within this interval. The other nine hybrids all exhibited patterns similar to either micro21D or Q1X, with distinct junctional fragments allowing identification of a fragile X-associated breakpoint cluster region (FXBCR) with this 7.4 kb fragment.

Figure 6:
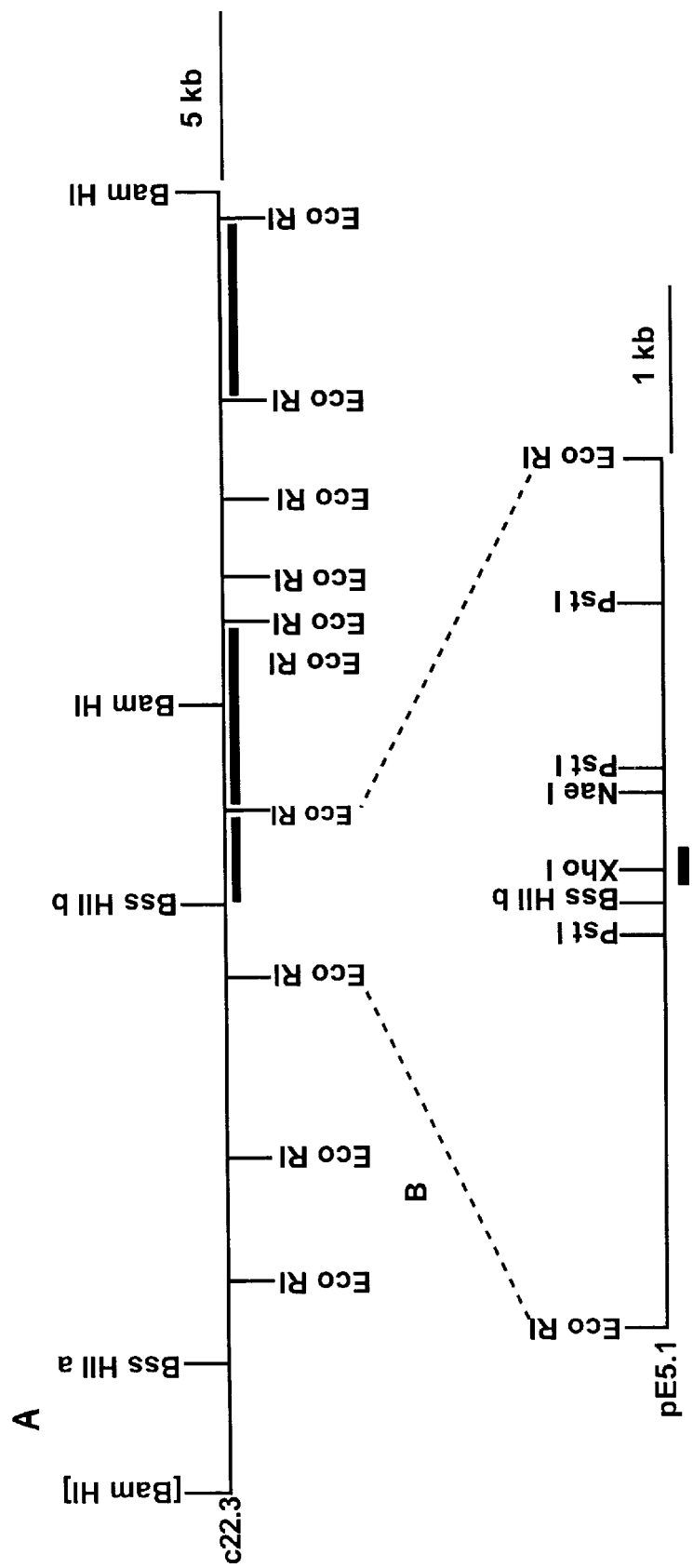
FIGS. 6A and 6B depict a restriction map of cosmid 22.3 and pE5.1. In (A) is cosmid 22.3 showing BssH II sites a and b as well as EcoR I and BamH I sites. The BamH I site in parentheses was destroyed during cloning. The solid lines below the map show fragments which hybridize to cDNAs BC72 and BC22. In (B) is the map of the cloned 5.1 kb EcoR I fragment of cosmid 22.3 (pE5.1). The solid line below the map shows the position of the FMR-1 exonic sequence which contains the Xho I site.

The 7.4 kb EcoR I fragment observed above on the fragile X chromosome was not observed in restriction digests of the overlapping cosmids 22.3 and 31.4. However, comparison of the cosmid restriction maps with the EcoR I fragments detected by c22.3 show a 5.1 kb fragment in the cosmids that is absent in Y75-1B-M1 and replaced by the 7.4 kb fragment. As shown in FIG. 6A, this 5.1 kb fragment contains the BssH II site b exhibiting fragile X specific hypermethylation. This fragment was subcloned from c31.4 and used to analyze hybrid breakpoints. As shown in FIG. 5B, the 5.1 kb fragment (pE5.1; FIG. 6B) hybridizes specifically to the 7.4 kb EcoR I fragment of the fragile X chromosome and clearly shows the junctional fragments in micro21D and Q1X. Thus a fragment length difference exists between the normal DNA used to construct YAC 209G4 and the fragile X chromosome of hybrid Y75-1B-M1, and this fragment identifies the FXBCR.

EXAMPLE 12

Fragile X Breakpoint Cluster Region Rearranged in Fragile X Patients

Figure 7:
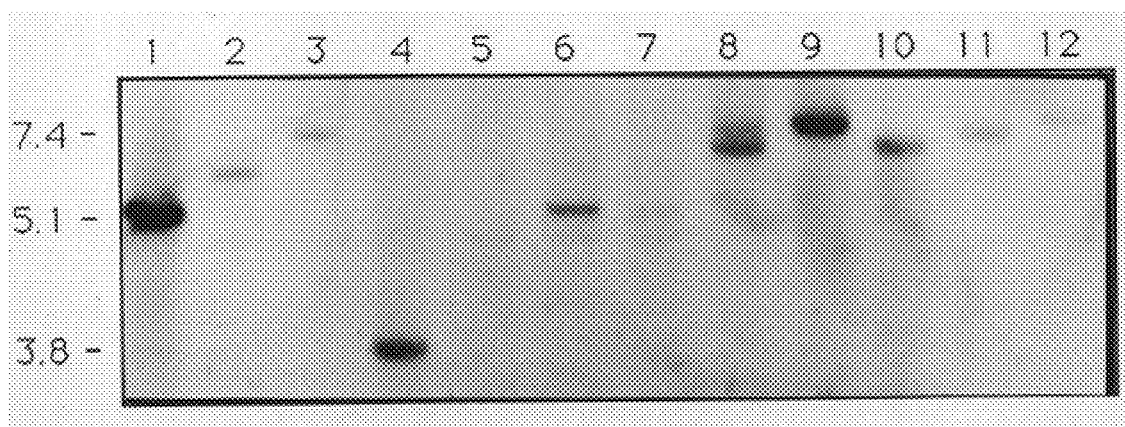
FIG. 7 shows length variation of EcoRI fragments from normal and fragile X human chromosomes with probe pE5.1.

The results of Southern hybridization of EcoR I digested DNA from two normal and seven unrelated fragile X individuals using pE5.1 as probe are shown in FIG. 7. In FIG. 7, Lanes 1, 6 and 7 demonstrate hybridization of the normal 5.1 kb EcoR I fragment in placental DNA (lane 1) and cloned into a cosmid (22.3) or YAC vector (209G4) and seeded into hamster DNA at single-copy level. Somatic cell hybrids containing portions of fragile X chromosomes in hamster backgrounds show bands of altered size from the normal 5.1 kb fragment. Lane 2 contains the hybrid X3000-11.1. Lane 3 contains DNA from micro28D, a proximal hybrid with a breakpoint distal to the fragile site and lane 4 contains DNA from miceo21D, a proximal hybrid with the same chromosome as micro28D, however with a breakpoint detected by pE5.1. Lane 5 contains hamster DNA. Lanes 8–12 contain DNA from 5 unrelated fragile X patients' lymphoblastoid lines. The bands altered from the normal 5.1 kb are seen in each fragile X sample.

The normal samples (two of five normal samples are shown) exhibit the expected 5.1 kb fragment while all seven fragile X patient DNAs exhibited larger EcoR I fragments with variable increases in size, including the 7.4 kb fragment observed from hybrid Y75-1B-M1. These data suggest an insertion or amplification event within the normal 5.1 kb fragment that is specific for the fragile X chromosome and is coincident with the fragile X-associated breakpoint cluster region and the fragile X-related CpG island.

EXAMPLE 13

Identification and Characterization of FMR-1

Figure 8:
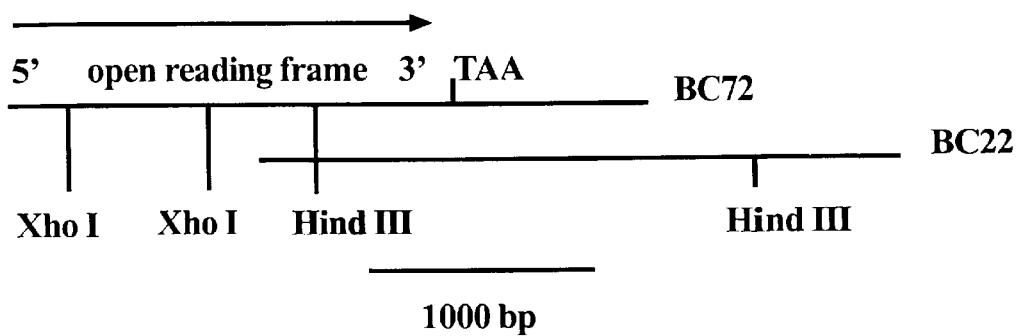
FIG. 8 is a map of the FMR-1 cDNA clones.

In order to search for transcripts associated with the fragile X region, the cosmid subclones of YAC 209G4 were used as hybridization probes to screen a cDNA library derived from normal human fetal brain RNA. Cosmid 4.1, containing BssH II site c (FIG. 4B), identified cDNA clone BC22. A map of FMR-1 cDNA clones is shown in FIG. 8. Restriction digestion and sequence analysis revealed an insert in BC22 of 2835 bp at location 934 to 3765 of SEQ ID NO: 1, with an open reading frame at one end extending 1033 bp to a stop codon. Since the reading frame remains open at the 5' end of the clone, BC22 was used to identify related cDNAs from the same library. Several overlapping clones were isolated, one of which, BC72, was characterized in greater detail. This clone extended the cDNA sequence another 933 bp in the 5' direction, and overlapped BC22 for approximately 2000 bp toward the 3' end. Sequence analysis demonstrated that the same reading frame remained open through the 5' end of BC72, indicating that the 5' end of the mRNA has not yet been reached, and allowing prediction of a portion (657 amino acids) of the encoded protein. It remains unclear if the entire 3' portion also was isolated since no poly(A) tract was found at the end of BC22, however a putative polyadenylation addition signal is observed in position 3741 following numerous in frame stop codons. In SEQ ID NO: 1, nucleotides 1–1027 derive from BC72 and nucleotides 934–3765 are from BC22.

A repeated DNA sequence is found close to the 5' end of BC72 with 28 CGG triplets interspersed with two AGG triplets. This CGG repeat encoding 30 contiguous arg residues begins with base 37 and extends to base 127. In the predicted open reading frame, this repeat would generate a protein domain composed of 30 contiguous arginine residues. Homology searches with the predicted protein sequence identify significant overlaps with a number of arginine-rich proteins, although none contain a polyarginine stretch of equivalent length. The remainder of the protein shows no significant homology in protein database searches. However, searches against DNA sequence databases identify several related sequences, the strongest of which is with the human androgen receptor (AR). This is an X-linked gene (mapping to Xq12) with an identical, though smaller, CGG repeat in the first exon which encodes a polyglycine stretch.

EXAMPLE 14
Northern Hybridization

Figure 9:
FIG. 9 is a Northern blot analysis of a poly(A)RNA hybridized with cDNA BC22.

Northern hybridization using the BC22 insert as probe was run. (FIG. 9). Five μg of poly(A) selected RNA from human brain (lane 1) and normal placenta (lane 2) were electrophoresed, blotted onto a GeneScreen Plus filter and hybridized with radiolabeled BC22 insert. A single hybridizing species of approximately 4.8 kb is observed in each lane. As seen in FIG. 9, this procedure detects a mRNA of approximately 4.8 kb in human brain and placenta. This indicates that the 3.8 kb of cDNA obtained does not contain the entire mRNA of this gene. The probe failed to detect signal in human liver, fetal lung and fetal kidney but did detect message in lymphocytes.

EXAMPLE 15
Zoo Blot Analysis

Figure 10:
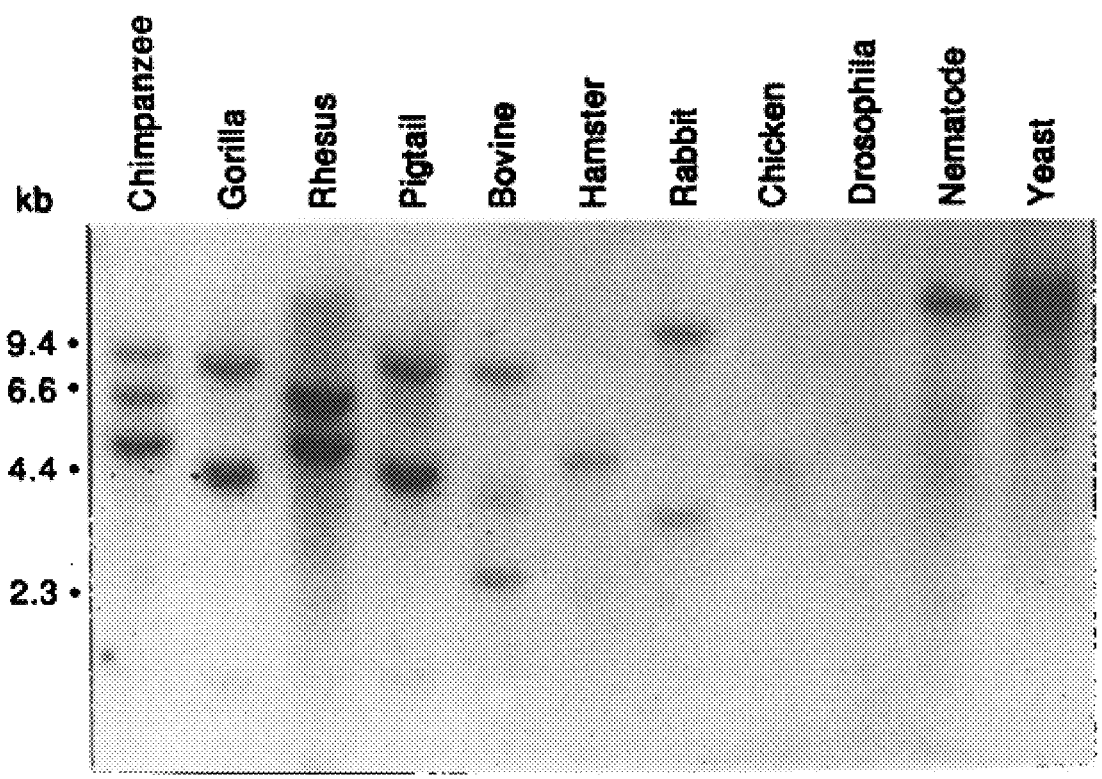
FIG. 10 is a zoo blot analysis of DNA isolated from several species hybridized with cDNA BC22.
Figure 12:
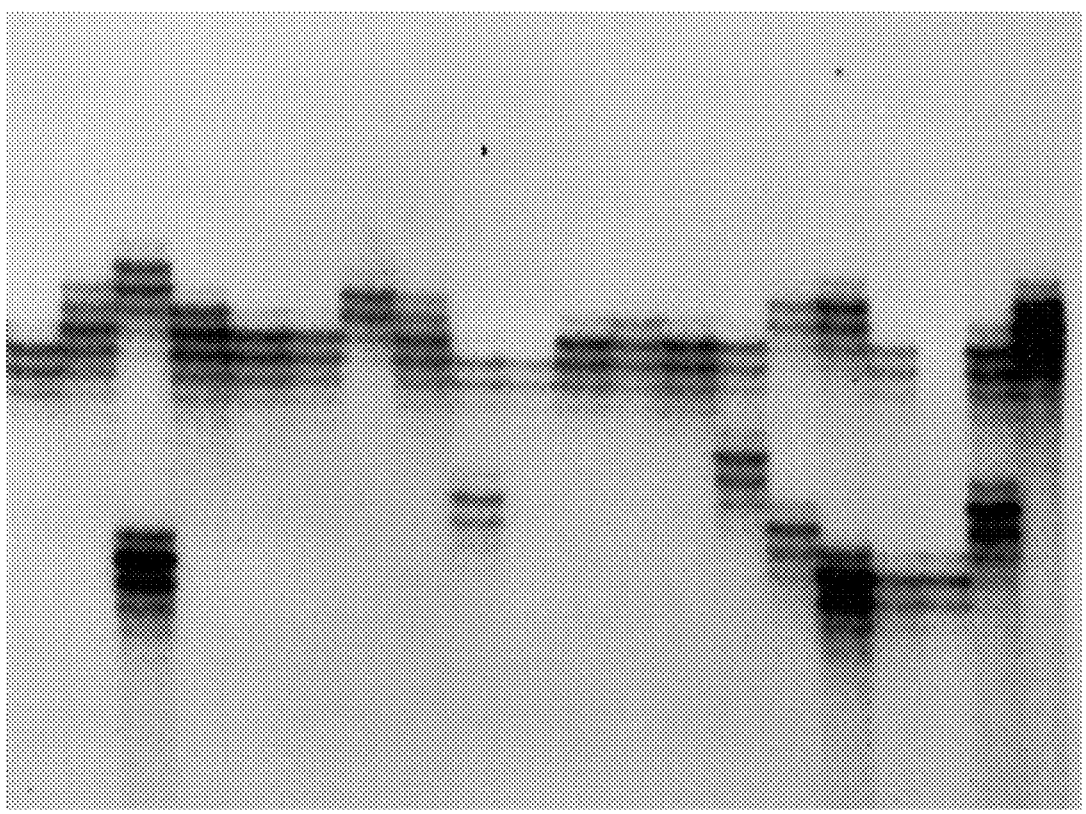
FIG. 12 shows the polymorphic nature of the "CGG" locus in normal human genomic DNAs. Genomic DNA was obtained from unrelated volunteer donors at a local blood bank.
Figure 13:
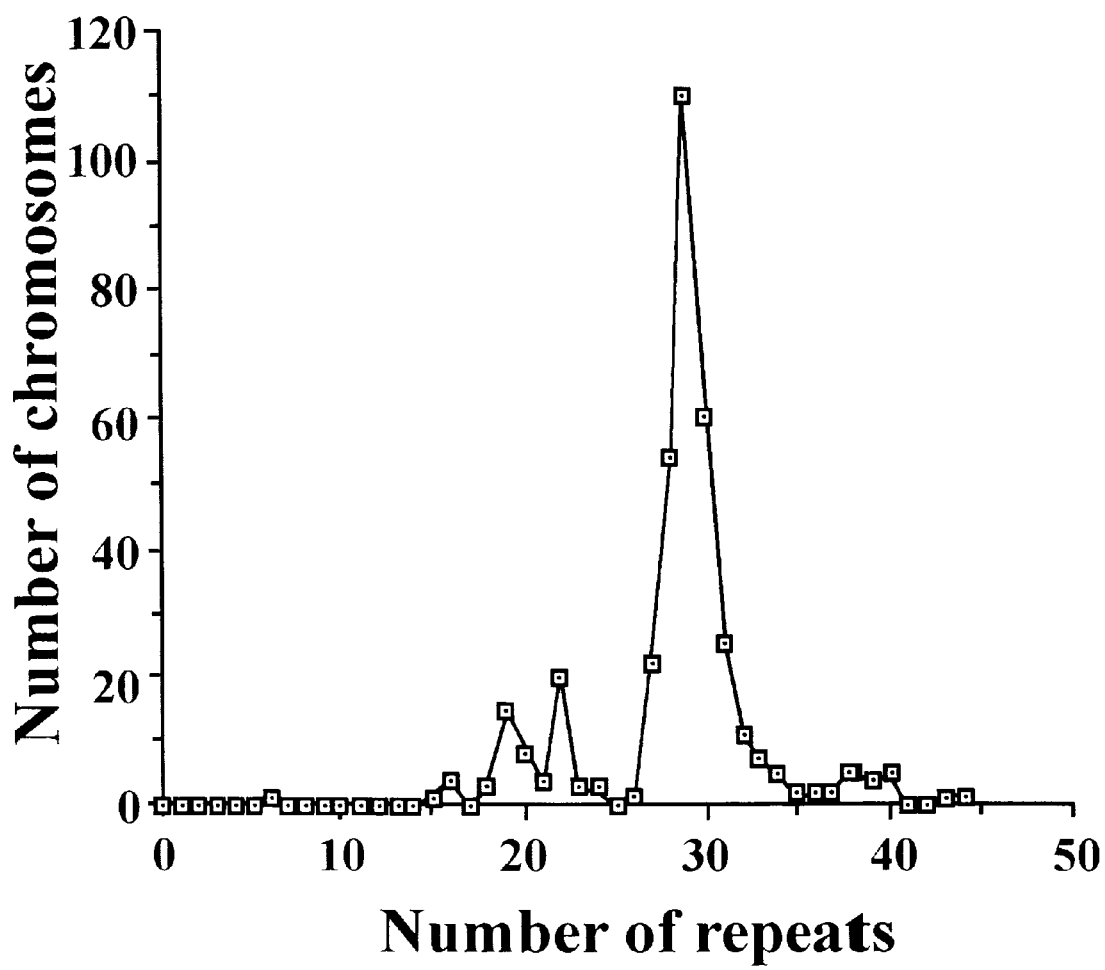
FIG. 13 shows the distribution of different fragile X alleles among the normal population. No obvious difference was observed for the pattern of distribution among different races (Caucasian, Black, Hispanic and Asian).

Hybridization of BC22 to DNA samples isolated from a number of different organisms was run (FIG. 10). Ten μg of DNA from each species was cleaved with EcoRI and electrophoresed and blotted onto a nylon membrane. Hybridization was carried out with labelled cDNA overnight using standard conditions and washed to a final stringency of 0.2× SSC for 5 min at 65° C. Hybridization signals were observed with all organisms with the exception of *Drosophila melanogaster*. Since this blot was washed under very stringent conditions (final wash in 0.2× SSC at 65° C. for 5 min), cross hybridization may be observed in Drosophila under less stringent conditions. However, the high stringency of the final wash does indicate the highly conserved nature of this sequence particularly in *C. elegans*.

EXAMPLE 16
Location of FMR-1 Gene Relative to the Fragile X-Related CpG Island and FXBCR BC22 demonstrates hybridization to the 70 kb fragment of YAC 209G4 between BssH II sites b and c as well as to cosmids 4.1, 34.4, 31.4 and 22.3 (FIG. 4), indicating exons spanning over 80 kb of DNA. The proximal/distal orientation of the transcript was determined by hybridizing end fragments of BC22 to the cosmid contig. Since the 3' end of BC22 detected cosmid 4.1 and the 5' end detected cosmid 22.3, the transcriptional orientation was distal from BssH II site b toward the Xq telomere. This suggests the potential involvement of the fragile X-related CpG island in the regulation of this gene. A 1 kb 5' fragment of BC72 (to the Hind III site at position 1026 of SEQ ID NO: 1) was used to study the location of the exons encoding this portion of the mRNA in the cosmid and YAC clones. In cosmid 22.3, this probe identifies three EcoR I fragments (FIG. 6A) distal to the BssH II site b. One of the fragments contains the BssH II site (b) as well as the breakpoint cluster region and exhibits length variation in fragile X patients. Restriction mapping and direct sequencing of the 5.1 kb EcoR I fragment using a primer derived from BC72 sequence (position 223 to 246) demonstrated an exon immediately distal to the BssH II site b. This exon contains an Xho I site (position 137 in FMR-1 cDNA sequence) that is found 310 nucleotides from the BssHII II site in genomic DNA (FIG. 6B). This exon also contains the block of CGG repeats which are seen in the sequence analysis of the genomic DNA as well. Thus the CGG repeat block is found within the fragile X-related CpG island and constitutes a portion of this CpG-rich region.

EXAMPLE 17
A PCR Assay to Determine Fragile X Disease

A PCR based test is devised in which the length of genomic DNA at the fragile X site from an individual is determined. In this method the total DNA was extracted from lymphoblastoid cells from fragile X and normal individuals. Oligonucleotide primers (SEQ ID NO: 10 and SEQ. ID. No. 11) were used in PCR using the following conditions: 94° C. 1 min. 72° 2 min. for 50 cycles and a 7 min final extension at 72° C. The use of 10% dimethylsulfoxide in the reaction is important for enhancing the ability to amplify this GC-rich sequence. The PCR products are visualized after size separation by electrophoresis using ethidium bromide staining. Differences in size between PCR products from normal and fragile X samples are observed, and these correspond to variation in the number of CGG repeats present.

Alternative conditions using oligonucleotide primers (SEQ ID NO: 10 and SEQ ID NO: 11) can be used in PCR: 95° C. for 10 min. for initial denaturation, followed by 25 cycles of DNA reannealing (65° C., 1 min.), elongation (72° C., 2 min.), and denaturation (95° C., 1.5 min.). The reaction contains 100 ng of test DNA, 3 pmoles of each primer, 10 mM Tris-HCl pH 8.3, 50 mM KCl, 2 mM $MgCl_2$, 200 uM dATP, 200 uM dCTP, 200 uM dTTP, 50 uM dGTP, 150 uM 7-deaza-dGTP, 10% DMSO, 2–4 uCi of $^{32}$P-dCTP and 0.45 units of Ampli-Taq DNA polymerase in a 15 ul volume. To visualize results of these assays, radioactive PCR products were heated to 95° C. for 2 min., then separated on a denaturing DNA sequencing gel (acrylamide). Alleles are sized relative to a sequencing ladder derived from bacteriophage M13, and the size differences are taken to correspond to the number of CGG repeats present. The range of repeats in the normal population is from 4–46, with a mean number of 29. In some fragile X chromosomes, the number of repeats can be assayed, and is between 50 and about 150. At present when there are greater than about 150 repeats these assay conditions do not amplify the fragile X chromosome. The use of 7-deaza dGTP, DMSO, high annealing and denaturing temperatures and $^{32}$P for detection are all important parameters for the success of these reactions. Lack of amplification in males, or amplification of only one of the two expected alleles in females with this protocol is taken as an indication of the presence of the fragile X mutation. A pair of oligonucleotide primers capable of acting as an internal control for amplification under these conditions has been derived from the human androgen receptor gene (Xq11-q12) (SEQ ID NO 21 and SEQ ID NO 22). A product is obtained from these primers in all the negative fragile X patients tested.

Results from five unrelated fragile X families are shown. B6 and D3 are affected females and C2 has been clinically diagnosed as "slow".

Consistent length amplification products were obtained in multiple assays of the same allele in the same sample and in multiple generations in pedigrees (FIG. 14) indicating that this PCR assay is faithful to the genomic organization and that the normal number of CGG repeats appears stable in meiosis.

Figure 14:
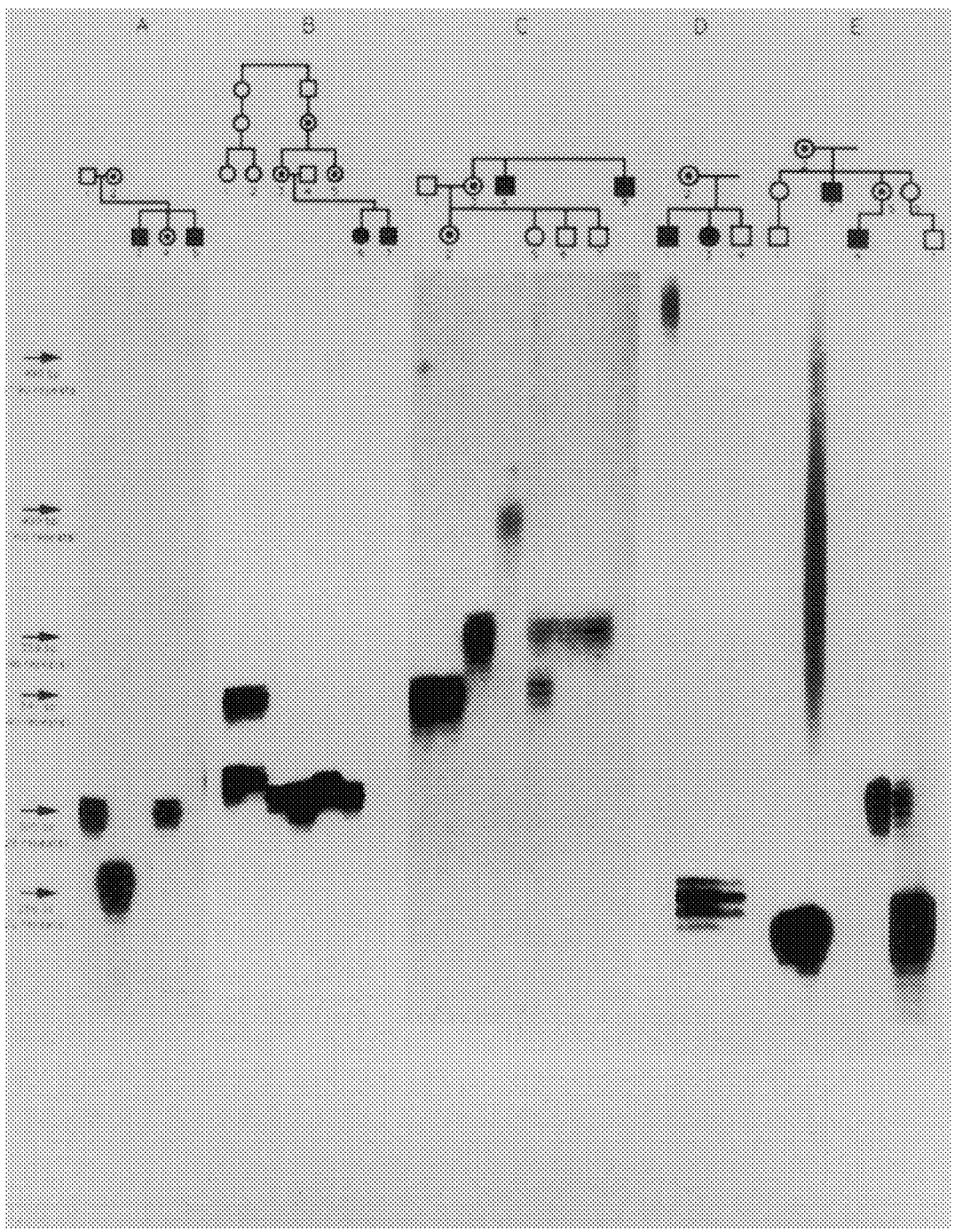
FIGS. 14A–14E represent a PCR study of CGG repeats in fragile X families. Lymphoblastoid cell line DNA was used for these analyses.

This PCR assay in fragile X families was capable of identifying all alleles of normal length, as well as some alleles of increased length (FIG. 14). In general, all affected males failed to amplify. This is not surprising given the presence of large (1000–2000 bp) length increases present in these individuals. Two affected males (FIG. 14, C4 and D1) did yield PCR products which are larger than normal (60 and >100 repeats). These individuals are mosaic by Southern hybridization, with EcoRI fragments of near normal length when assayed with pE5.1. Thus, all affected males give abnormal results (no amplification or larger than normal). Flanking region amplification of all affected males indicates that the null result obtained for the CGG assay is not due to technical difficulties or deletion. For some female carriers (A2, A4, C3, D2 and E5), only one normal allele can be detected by PCR while the other allele is too large to amplify. These results were further confirmed by Southern blot analysis. In family A, the daughter A4 was cytogenetically diagnosed as a normal female. However, the PCR assay indicated that she is indeed a carrier, having inherited the maternal fragile X allele. This is an example where the PCR based method can be a powerful diagnostic assay for carriers.

Normal transmitting males (NTM) and their daughters exhibit abnormal sized products when the CGG region is assayed. These products are 69–220 bp larger than the average normal product, suggesting repeats numbering between 52 and 100 CGGs. For female carriers (B3, B5, and E2) who are daughters of NTMs, the normal allele is accompanied by a mutant allele approximately 200 bp larger than the normal. These premutation alleles can be stably inherited (see FIG. 14, family B). In the case of family E, the carrier mother E4 has a normal allele and a 200 bp larger allele. Her daughter E5 received one normal allele presumably from her father and one abnormal allele much larger than her mother's according to Southern blot analysis. Her son (E4) has an even larger allele and is penetrant for fragile X syndrome. This is a case where amplification events occurred through more than one generation before phenotypic expression.

EXAMPLE 18
Elucidation of Fragile X Site

To elucidate the fragile X site at the molecular level, somatic cell hybrids were isolated that contained translocations between rodent chromosomes and the human fragile X chromosome, retaining either human Xpter-q27.3 or human Xq27.3-qter, referred to as proximal or distal translocations, relative to the fragile X site. Since the high frequency and specificity of the chromosome breakage was not observed in normal X hybrids and since the translocation breakpoints map within the same interval defined by polymorphic loci which flank the fragile X locus, these breakpoints are likely to coincide with the fragile X site.

A yeast artificial chromosome (YAC) has been isolated which spans some of these translocation breakpoints and includes polymorphic loci which flank the fragile X locus. Within this region, a fragile X-related CpG island was identified which is aberrantly hypermethylated in patients and most carriers of the fragile X syndrome. Although the significance of this CpG-island hypermethylation remains unclear, these data do imply the presence of a gene, perhaps inactivated by methylation, within a genomic region which includes the fragile X-associated hybrid breakpoints.

EXAMPLE 19
PCR-Based Assay for Methylation at the Fragile X-Associated CpG Island A PCR-based test is devised in which the methylation status of the genomic DNA at the fragile X site from an individual is determined. In this method the total DNA is extracted from lymphoblastoid cells or whole blood from normal and fragile X individuals. The DNA is then subjected to digestion with a methylation-sensitive restriction endonuclease such as BssH II. Both digested and undigested DNAs are then subjected to PCR. Oligonucleotide primers (SEQ ID NO: 19 and SEQ ID NO: 20) were used in PCR under the following conditions: 95° C. for 10 min. for initial denaturation, followed by 35 cycles of DNA reannealing (65° C., 1 min.), elongation (72° C., 2 min.), and denaturation (95° C., 1.5 min.). The reaction contains 100 ng of test DNA, 10 pmoles of each primer, 10 mM Tris-HCl pH 8.3, 50 mM KCl, 2 mM $MgCl_2$, 200 uM dATP, 200 uM dCTP, 200 uM dTTP, 200 uM dGTP, 10% DMSO, and 1.5 units of Ampli-Taq DNA polymerase in a 50 ul volume. Detection of the amplification products is accomplished by agarose gel electrophroesis and staining with ethidium bromide. The presence of a PCR product in digested samples is indicative of methylation at the restriction cleavage site. Amplification of undigested samples serves as a control—the absence of amplification in the digested sample indicates no methylation at the site.

Figure 15:
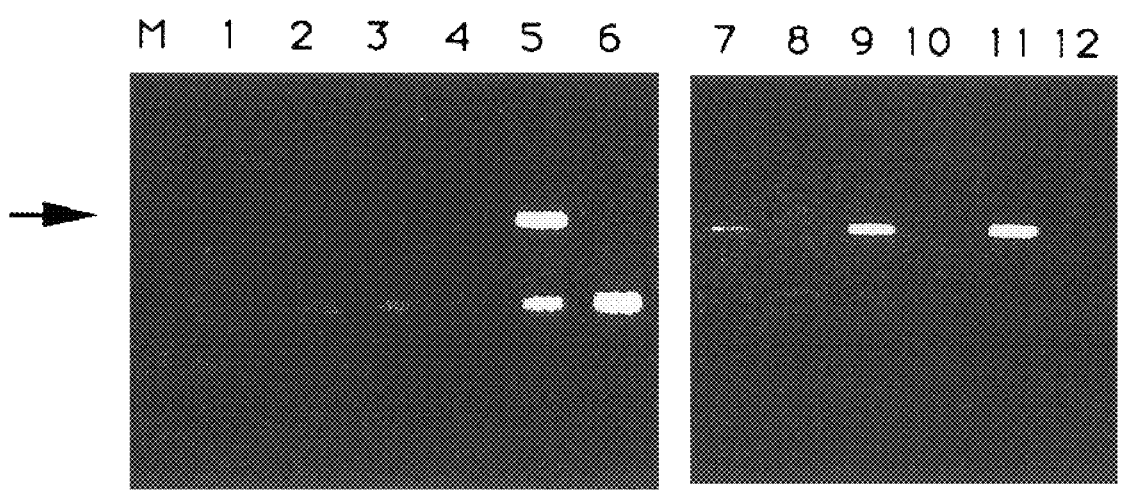
FIG. 15 shows the methylation status of normal and affected male DNAs tested by PCR. Lanes 1–6 are patient DNAs and lanes 7–12 are normal DNAs. Genomic DNAs were digested to completion by BssHII.200 ng of undigested (odd numbered lanes) or digested (even numbered lanes) DNA was was used for PCR amplification. The conditions for the PCR reactions were those described in FIG. 1. The PCR products were examined on a 2% agarose gel and stained with ethidium bromide.

FIG. 15 shows the methylation status of normal and affected male DNAs tested by PCR. Lanes 1–6 are patient DNAs and lanes 7–12 are normal DNAs. Genomic DNAs were digested to completion by BssH II. 200 ng of undigested (odd numbered lanes) or digested (even numbered lanes) DNA was used for PCR amplification. The conditions for the PCR reactions were those described in the example. The PCR products were examined on a 2% agarose gel and stained with ethidium bromide.

PCR products are obtained from male patient DNAs, but not from normal DNAs after digestion with BssH II. Examples of 3 normal and 3 affected males are shown in FIG. 15. While not useful in females due to methylation of this CpG island on the inactive X chromosome, this test in conjunction with the CGG assay represents a rapid and simple screen for fragile X males.

EXAMPLE 20
PCR-Bassed Assay for the Integrity of the Sequences Surrounding the CGG Repeat A PCR-based test is devised in which the length of the genomic DNA at the fragile X site from an individual is determined. In this method the total DNA is extracted from lymphoblastoid cells or whole blood from normal and fragile X individuals. Oligonucleotide primers (SEQ ID NO: 15 and SEQ ID NO: 16) or primers (SEQ ID NO: 10 and SEQ ID NO: 17) or primers (SEQ ID NO: 11 and SEQ ID NO: 18) were used in PCR under the following conditions:

95° C. for 10 min. for initial denaturation, followed by 50 cylces of DNA reannealing (65° C., 1 min.), elongation (72° C., 2 min.), and denaturation (95° C., 1.5 min.). The reactions contains 100 ng of test DNA, 10 pmoles of each primer, 10 mM Tris-HCl pH 8.3, 50 mM KCl, 2 mM $MgCl_2$, 200 uM dATP, 200 uM dCTP, 200 uM dTTP, 200 uM dGTP, 10% DMSO, and 1.5 units of Ampli-Taq DNA polymerase in a 50 ul volume. Detection of the amplification products is accomplished by agarose gel electrophoresis and staining with ethidium bromide. Alternatively, the inclusion of $^{32}P$ and detection via autoradiography can be employed. Presence of a product of the expected length is indicative of normal sequence composition between primer binding sites. No alterations have been observed in fragile X individuals. These assays can serve as controls for the CGG alterations inferred from negative PCR results obtained with primers (SEQ ID NO: 10 and SEQ ID NO: 11).

All patents and publications mentioned in this specification are indicative of the levels of those skilled in the art to which the invention pertains. All patents and publications are herein incorporated by reference to the same extent as if each individual patent or publication was specifically and individually indicated to be incorporated by reference.

One skilled in the art will readily appreciate that the present invention is well adapted to carry out the objects and attain the ends and advantages mentioned as well those inherent therein. The sequences, methods, procedures and techniques described herein are presently representative of the preferred embodiments and are intended to be exemplary and not intended as limitations on the scope. Changes therein and other uses which are encompassed within the spirit of the invention or defined by the scope of the appended claims will occur to those skilled in the art.

What is claimed is:

1. A method of detecting a mutation for fragile X syndrome comprising the step of measuring and comparing the expression of the FMR-1 gene in normal and affected individuals, wherein variation in the expression in affected individuals compared with that in normal individuals indicates a mutation for the fragile-X syndrome.

2. The method of claim 1 wherein the expression is measured by determining the amount of FMR-1 mRNA expressed.

3. The method of claim 2, wherein the amount of mRNA is determined by the steps of:

extracting RNA from affected individuals to be tested and normal individuals;

preparing FMR-1 cDNA and control gene cDNA from said extracted RNA;

quantifying the FMR-1 cDNA by comparing the amount of FMR-1 cDNA with the amount of control gene cDNA; and comparing the variation in the amount of FMR-1 cDNA from tested individuals with the amount of FMR-1 cDNA in normal individuals, wherein variation in the amount of FMR-1 cDNA from affected individuals compared with that in normal individuals indicates a mutation for the fragile X syndrome.

4. The method of claim 3, wherein the quantification step includes PCR of the FMR-1 cDNA, PCR of the control gene cDNA, electrophoresis of the PCR products, ethidium bromide staining of the products and quantification of FMR-1 products versus control gene products.

5. The method of claim 4, wherein the oligonucleotide primers SEQ ID NO: 8 and SEQ ID NO: 9 are used to amplify the cDNA from the fragile X site.

6. The method of claim 5, wherein the control gene is HPRT and the oligonucleotide primers are SEQ ID NO: 12 and SEQ ID NO: 13.

7. The method of claim 1, wherein the expression is measured by determining the amount of predicted FMR-1 protein.

8. The method of claim 7, wherein the predicted FMR-1 protein is SEQ ID NO: 14.

9. A 657 amino acid peptide sequence of protein FMR-1 having the sequence of SEQ ID NO: 14.

* * * * *